US010799555B2

(12) United States Patent
Gutierrez et al.

(10) Patent No.: US 10,799,555 B2
(45) Date of Patent: Oct. 13, 2020

(54) PD-1 PEPTIDE INHIBITORS

(71) Applicant: Leidos, Inc., Reston, VA (US)

(72) Inventors: Gabriel M. Gutierrez, Reston, VA (US); Vinayaka Kotraiah, Reston, VA (US); James Pannucci, Reston, VA (US); Ramses Ayala, Reston, VA (US)

(73) Assignee: Leidos, Inc., Reston, VA (US)

( * ) Notice: Subject to any disclaimer, the term of this patent is extended or adjusted under 35 U.S.C. 154(b) by 335 days.

(21) Appl. No.: 15/906,481

(22) Filed: Feb. 27, 2018

(65) Prior Publication Data

US 2018/0200328 A1 Jul. 19, 2018

Related U.S. Application Data

(63) Continuation-in-part of application No. 15/705,333, filed on Sep. 15, 2017, now Pat. No. 10,098,950.

(60) Provisional application No. 62/395,195, filed on Sep. 15, 2016.

(51) Int. Cl.
| | | |
|---|---|---|
| *A61K 38/10* | (2006.01) | |
| *A61K 39/015* | (2006.01) | |
| *A61K 38/16* | (2006.01) | |
| *A61K 39/00* | (2006.01) | |
| *A61K 35/17* | (2015.01) | |
| *A61K 38/19* | (2006.01) | |
| *A61P 33/06* | (2006.01) | |
| *A61P 31/20* | (2006.01) | |
| *A61P 37/04* | (2006.01) | |
| *A61P 35/04* | (2006.01) | |
| *A61K 45/06* | (2006.01) | |
| *C07K 7/08* | (2006.01) | |
| *C07K 14/00* | (2006.01) | |
| *A61K 39/39* | (2006.01) | |
| *A61K 48/00* | (2006.01) | |

(52) U.S. Cl.
CPC .............. *A61K 38/10* (2013.01); *A61K 35/17* (2013.01); *A61K 38/16* (2013.01); *A61K 38/19* (2013.01); *A61K 39/0011* (2013.01); *A61K 39/015* (2013.01); *A61K 39/39* (2013.01); *A61K 45/06* (2013.01); *A61P 31/20* (2018.01); *A61P 33/06* (2018.01); *A61P 35/04* (2018.01); *A61P 37/04* (2018.01); *C07K 7/08* (2013.01); *C07K 14/00* (2013.01); *A01K 2227/105* (2013.01); *A01K 2267/0331* (2013.01); *A01K 2267/0337* (2013.01); *A61K 48/00* (2013.01)

(58) Field of Classification Search
None
See application file for complete search history.

(56) References Cited

U.S. PATENT DOCUMENTS

| | | |
|---|---|---|
| 10,098,950 B2 | 10/2018 | Gutierrez et al. |
| 2002/0111323 A1 | 8/2002 | Martin et al. |
| 2011/0318373 A1 | 12/2011 | Sasikumar et al. |
| 2013/0237580 A1 | 9/2013 | Sasikumar et al. |
| 2015/0125955 A1 | 5/2015 | Chomont et al. |
| 2017/0274074 A1 | 9/2017 | Das-Young et al. |

FOREIGN PATENT DOCUMENTS

| | | |
|---|---|---|
| CN | 107383174 A | 11/2017 |
| WO | 2012168944 A1 | 12/2012 |
| WO | 2013144704 A1 | 10/2013 |
| WO | 2014127917 A1 | 8/2014 |
| WO | 2018053218 A1 | 3/2018 |

OTHER PUBLICATIONS

International Search Report and Written Opinion for PCT/US2018/020209, dated Oct. 22, 2018, 17 pages.
Phares et al., "Enhancement of the immune response to plasmodium yoelii circumsporozoite protein by PD-1 inhibitors," Amer. J. Tropical Med. and Hygiene 97, Abstract No. 1062, Nov. 1, 2017, 1 page.
Adams et al., "Big opportunities for small molecules in immuno-oncology," Nature Reviews Drug Discovery Advance Online Publication, Jul. 31, 2016, 20 pages.
Bruno et al., "Basics and recent advances in peptide and protein drug delivery," Ther. Deliv. 4, 1443-67, 2013.
Bu et al., "Learning from PD-1 Resistance: New Combination Strategies," Trends Mol. Med. 22, 448-51, 2016.
Burnett & Rossi, "RNA-based Therapeutics—Current Progress and Future Prospects," Chem Biol. 19, 60-71, 2012.
Cao, "Advances in Delivering Protein and Peptide Therapeutics," Pharmaceutical Technology 40, 22-24, Nov. 2, 2016.
Chang, Hao-Nan, et al., "Blocking of the PD-1/PD-L1 Interaction by a D-Peptide Antagonist for Cancer Immunitherapy," Angewandte Chemie International Edition, vol. 54, No. 40, 11760-11764, Aug. 10, 2015.
Cherkassky et al., "Human CAR T cells with cell-intrinsic PD-1 checkpoint blockade resist tumor-mediated inhibition," J. Clin. Invest. 126, 3130-44, 2016.

(Continued)

*Primary Examiner* — Alana Harris Dent

(74) *Attorney, Agent, or Firm* — Banner & Witcoff, Ltd.

(57) ABSTRACT

This disclosure provides peptides which have a strong affinity for the checkpoint receptor "programmed death 1" (PD-1). These peptides block the interaction of PD-1 with its ligand PD-L1 and can therefore be used for various therapeutic purposes, such as inhibiting the progression of a hyperproliferative disorder, including cancer; treating infectious diseases; enhancing a response to vaccination; treating sepsis; and promoting hair re-pigmentation or lightening of pigmented skin lesions.

2 Claims, 33 Drawing Sheets

Specification includes a Sequence Listing.

(56) References Cited

OTHER PUBLICATIONS

Chong et al., "PD-1 blockade modulates chimeric antigen receptor (CAR)-modified T cells: refueling the CAR," Blood. 129(8), 1039-41, 2017, published on-line Dec. 28, 2016.
Creative Biolabs User Manual, "TriCo-20TM Phage Display 20-mer Random Peptide Library," 14 pages, Aug. 4, 2009.
Differding, "AUNP-12—A Novel Peptide Therapeutic Targeting PD-1 Immune Checkpoint Pathway for Cancer Immunotherapy—Structure Activity Relationships & Peptide/Peptidomimetic Analogs," available at http://www.differding.com/data/AUNP_12_A_novel_peptide_therapeutic_targeting_PD_1_immune_checkpoint_pathwayfor_cancer_immunotherapy.pdf, Feb. 26, 2014.
Duraiswamy et al., "Dual Blockade of PD-1 and CTLA-4 Combined with Tumor Vaccine Effectively Restores T-Cell Rejection Function in Tumors," Cancer Res 73, 3591-603, 2013.
Feridooni et al., "Noninvasive Strategies for Systemic Delivery of Therapeutic Proteins—Prospects and Challenges," Chapter 8 of Sezer, ed., Smart Drug Delivery System, available at http://www.intechopen.com/books/smart-drug-delivery-system, Feb. 10, 2016.
Gutierrez et al., International Search Report and Written Opinion for PCT/US2015/051697, 5 pages, searched Nov. 13, 2017, dated Dec. 1, 2017.
Gutierrez et al., PCT/US2015/051697 filed Sep. 15, 2017, 49 pages.
Gutierrez et al., U.S. Appl. No. 15/908,861 divisional application of U.S. Appl. No. 15/705,333, filed Mar. 1, 2018, 49 pages.
Gutierrez et al., U.S. Appl. No. 15/705,333, filed Sep. 15, 2017, 49 pages.
Gutierrez et al., U.S. Appl. No. 15/705,333 Interview Summary, Notice of Allowance, and Notice of Allowability dated Dec. 6, 2017, 18 pages.
Gutierrez et al., U.S. Appl. No. 15/705,333, amendment filed Feb. 28, 2018, 6 pages.
John et al., "Blockade of PD-1 immunosuppression boosts CAR T-cell therapy," OncoImmunology 2, e26286, 3 pages, 2013.
Kaczmarek et al., "Advances in the delivery of RNA therapeutics: from concept to clinical reality," Genome Medicine 2017; 9:60, 16 pages.
Kavikansky & Pavlick, "Beyond Checkpoint Inhibitors: The Next Generation of Immunotherapy in Oncology," Amer. J. Hematol. Oncol. 13, 9-20, 2017.
Kontermann, "Half-life extended biotherapeutics," Expert Opin. Biol. Ther. 16, 903-15, 2016.
Li et al., "Discovery of peptide inhibitors targeting human programmed death 1 (PD-1) receptor," Oncotarget 7, 64967-76, Aug. 12, 2016.
Magiera-Mularz et al., "Bioactive macrocyclic inhibitors of the PD-1/PD-L1 immune checkpoint," Angewandte Chemie Int. Ed. 10.1002/anie.201707707, e-published Sep. 26, 2017.
Maute et al., "Engineering high-affinity PD-1 variants for optimized immunotherapy and immuno-PET imaging," Proc. Natl. Acad. Sci. USA, E6506-E6514, published online Nov. 10, 2015.
Morrissey et al., "Immunotherapy and Novel Combinations in Oncology: Current Landscape, Challenges, and Opportunities," Clinical and Translational Science 9, 89-104, 2016.
Patel et al., "Recent Advances in Protein and Peptide Drug Delivery: A Special Emphasis on Polymeric Nanoparticles," Protein. Pept. Lett. 21, 1102-20, 2014.
Penchala et al., "A biomimetic approach for enhancing the in vivo half-life of peptides," Nat. Chem. Biol. 11, 793-98, 2015.
Rivera et al., "Hair Repigmentation During Immunotherapy Treatment With an Anti-Programmed Cell Death 1 and Anti-Programmed Cell Death Ligand 1 Agent for Lung Cancer," JAMA Dermatol. Jul. 12, 2017. doi: 10.1001/jamadermatol.2017.2106, Jul. 12, 2017.
Sharma & Allison, "Immune Checkpoint Targeting in Cancer Therapy: Toward Combination Strategies with Curative Potential," Cell 161, 205-14, 2015.
Shindo et al., "Combination Immunotherapy with 4-1BB Activation and PD-1 Blockade Enhances Antitumor Efficacy in a Mouse Model of Subcutaneous Tumor," Anticancer Res. 35, 129-36, 2015.
Skalniak et al., "Small-molecule inhibitors of PD-1/PD-L1 immune checkpoint alleviate the PD-L1-induced exhaustion of T-cells," Oncotarget, Advance Publications, Aug. 7, 2017, 15 pages.
Smith, "Pigmented skin lesions lightened during melanoma immunotherapy," http://www.mdedge.com/edermatologynews/article/132598/melanoma/pigmented-skin-lesions-lightened-during-melanoma, Mar. 2, 2017.
Tzeng et al., "PD-1 blockage reverses immune dysfunction and hepatitis B viral persistence in a mouse animal model," PLoS One 7(6):e39179, 2012.
Van Dessel et al., "Potent and tumor specific: arming bacteria with therapeutic proteins," Ther. Deliv. 6, 385-99, 2015.
Yang et al., "Oral vaccination with salmonella simultaneously expressing Yersinia pestis F1 and V antigens protects against bubonic and pneumonic plague," J Immunol. 178, 1059-67, 2007.
Ye et al., "T-cell exhaustion in chronic hepatitis B infection: current knowledge and clinical significance," Cell Death Dis. Mar. 19;6:e1694, 2015.
Young et al., "Co-inhibition of CD73 and A2AR Adenosine Signaling Improves Anti-tumor Immune Responses," Cancer Cell 30, 391-403, 2016.
Zarganes-Tzitzikas et al., "Inhibitors of programmed cell death 1 (PD-1): a patent review," Expert Opinion on Therapeutic Patents 26, 973-77, published on-line Jul. 6, 2016.
Zhan et al., "From monoclonal antibodies to small molecules: the development of inhibitors targeting the PD-1/PD-L1 pathway," Drug Discovery Today 21, 1027-36, Jun. 2016.

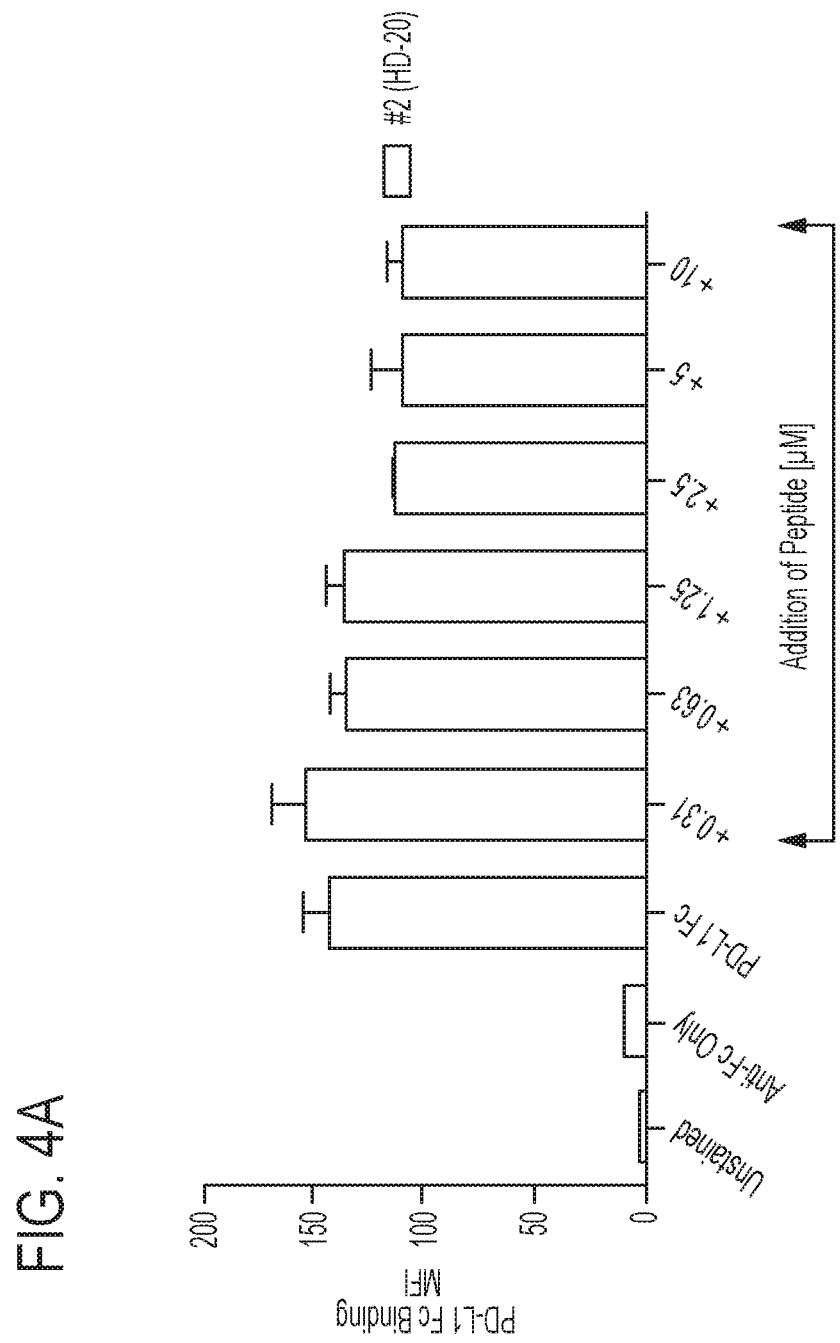

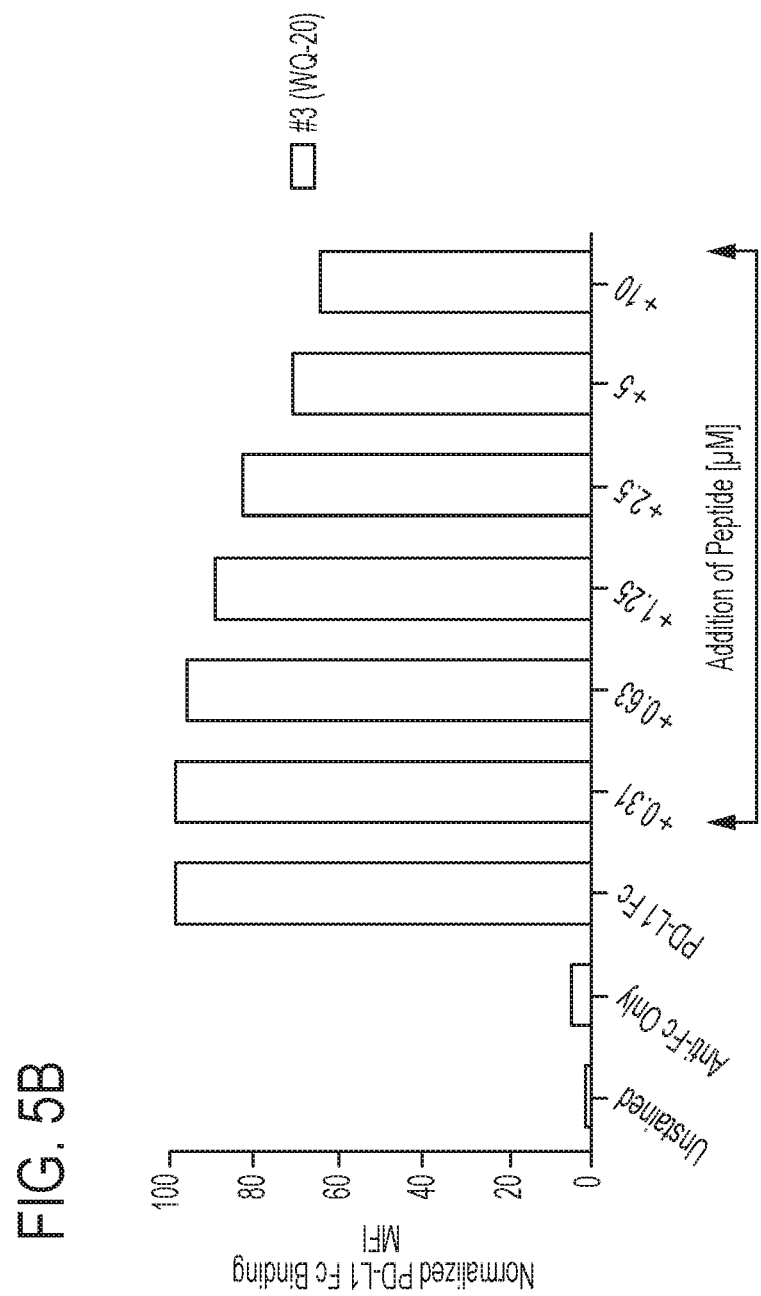

IFNgamma [pg/ml]

PD-1 PEPTIDE INHIBITORS

This application is a continuation-in-part of Ser. No. 15/705,333 filed on Sep. 15, 2017, which claims priority to and incorporates by reference in its entirety U.S. Ser. No. 62/395,195 filed on Sep. 15, 2016. Ser. No. 15/705,333, Ser. No. 62/395,195, and each reference cited in this disclosure are incorporated herein in their entireties.

This application incorporates by reference the contents of a 1.43 kb text file created on Feb. 27, 2018 and named "00047900252sequencelisting.txt," which is the sequence listing for this application.

TECHNICAL FIELD

This disclosure relates generally to immunomodulatory peptides.

BRIEF DESCRIPTION OF THE DRAWINGS

FIG. 3A, MFI; FIG. 3B, normalized mean fluorescence intensity (MFI).

FIGS. 4A-B. Graphs showing effect of peptide HD20 on binding of PD-L1 to PD-1. FIG. 4A, MFI; FIG. 4B, normalized MFI.

FIGS. 5A-B. Graphs showing effect of peptide WQ20 on binding of PD-L1 to PD-1. FIG. 5A, MFI; FIG. 5B, normalized MFI.

FIG. 6A, MFI; FIG. 6B, normalized MFI.

DETAILED DESCRIPTION

Figure 1:
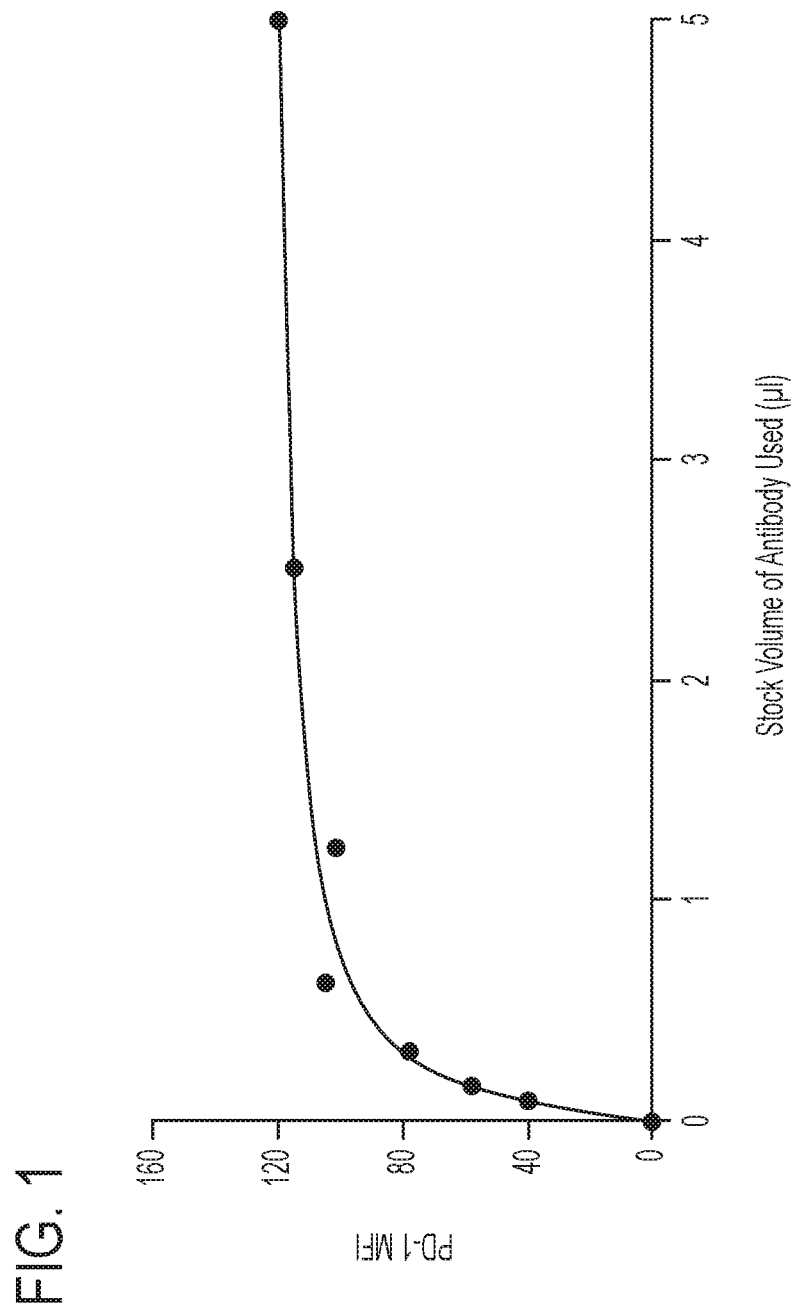
FIG. 1. Graph showing saturatable binding of anti-human PD-1 antibody to Jurkat cells.

This disclosure provides four peptides:

| peptide | amino acid sequence | SEQ ID NO: |
|---|---|---|
| QP20 | QTRTVPMPKIHHPPWQNVVP | 1 |
| HD20 | HHHQVYQVRSHWTGMHSGHD | 2 |

-continued

| peptide | amino acid sequence | SEQ ID NO: |
|---------|---------------------|------------|
| WQ20    | WNLPASFHNHHIRPHEHEWIQ | 3 |
| SQ20    | SSYHHFKMPELHFGKNTFHQ  | 4 |

These peptides share a core sequence of HH_, which is shown above in bold, and have a strong affinity for the checkpoint receptor "programmed death 1" (PD-1). These peptides block the interaction of PD-1 with its ligand PD-L1 and can therefore be used to inhibit the progression of a hyperproliferative disorder, including cancer, or to treat infectious diseases, including persistent infections by agents such as HIV, hepatitis B virus (HBV), hepatitis C virus (HCV), and *Plasmodium falciparum*, by enhancing, stimulating, and/or increasing an individual's immune response.

In some embodiments, any of the disclosed peptides can be modified using chemical or recombinant methods to enhance stability or other pharmacokinetic properties. See, e.g., US 2017/0020956. Modifications include, but are not limited to, replacement of one or more L-amino acid with its corresponding D-form, acetylation on a C- and/or N-terminal residue, amidation on a C- and/or N-terminal residue, cyclization, esterification, glycosylation, acylation, attachment of myristic or palmitic acid, addition of an N-terminal glycine, addition of lipophilic moieties such as long fatty acid chains, and PEGylation.

In some embodiments, one or more of the disclosed peptides can be conjugated to various moieties, such as albumin and transthyretin, to enhance the plasma half-life of the peptide(s). Methods of preparing such conjugates are well known in the art (e.g., Penchala et al., 2015; Kontermann, 2016; Zorzi et al., 2017).

In some embodiments, any of the disclosed peptides can be conjugated to a partner molecule, such as a peptide or protein such as an antibody intended to increase the half-life in vivo and/or to provide specific delivery to a target tissue or cell. Conjugation may be direct or can be via a linker. In some of these embodiments, the peptide can be modified to substitute one or more amino acids with amino acids used to attach partner molecules, such as lysine, or by N-terminal extension of the peptide with, e.g., 1, 2, 3, or 4 glycine spacer molecules.

Peptides, or modified versions of the peptides as described above, can be made by any method known in the art, including synthetic methods, recombinant methods, or both. Synthetic methods include solid-phase and solution methods, and may include the use of protective groups. See, e.g., Bodanszky et al. (1976), McOmie (1973), Merrifield (1963), Neurath et al. (1976), Stuart & Young (1984).

Recombinant production of peptides can be carried out using any nucleotide sequence(s) encoding the peptides in any suitable expression system. Nucleic acid molecules encoding one or more of the disclosed peptides can be incorporated into an expression cassette that includes control elements operably linked to the coding sequences. Control elements include, but are not limited to, initiators, promoters (including inducible, repressible, and constitutive promoters), enhancers, and polyadenylation signals. Signal sequences can be included. The expression cassette can be provided in a vector that can be introduced into an appropriate host cell for production of the peptide(s). Methods of constructing expression cassettes and expression vectors are well known. Expression vectors can include one or more of the expression cassettes described in the paragraphs below.

In some embodiments, an expression cassette encodes a peptide comprising the amino acid sequence SEQ ID NO:1. In some embodiments, an expression cassette encodes a peptide consisting essentially of the amino acid sequence SEQ ID NO:1. In some embodiments, an expression cassette encodes a peptide consisting of the amino acid sequence SEQ ID NO:1.

In some embodiments, an expression cassette encodes a peptide comprising the amino acid sequence SEQ ID NO:2. In some embodiments, an expression cassette encodes a peptide consisting essentially of the amino acid sequence SEQ ID NO:2. In some embodiments, an expression cassette encodes a peptide consisting of the amino acid sequence SEQ ID NO:2.

In some embodiments, an expression cassette encodes a peptide comprising the amino acid sequence SEQ ID NO:3. In some embodiments, an expression cassette encodes a peptide consisting essentially of the amino acid sequence SEQ ID NO:3. In some embodiments, an expression cassette encodes a peptide consisting of the amino acid sequence SEQ ID NO:3.

In some embodiments, an expression cassette encodes a peptide comprising the amino acid sequence SEQ ID NO:4. In some embodiments, an expression cassette encodes a peptide consisting essentially of the amino acid sequence SEQ ID NO:4. In some embodiments, an expression cassette encodes a peptide consisting of the amino acid sequence SEQ ID NO:4.

In some embodiments, an expression cassette encodes only two of the disclosed peptides; e.g., a peptide (a) a peptide comprising, consisting essentially of, or consisting of the amino acid sequence SEQ ID NO:1 and a peptide comprising, consisting essentially of, or consisting of the amino acid sequence SEQ ID NO:2; (b) a peptide comprising, consisting essentially of, or consisting of the amino acid sequence SEQ ID NO:1 and a peptide comprising, consisting essentially of, or consisting of the amino acid sequence SEQ ID NO:3; (c) a peptide comprising, consisting essentially of, or consisting of the amino acid sequence SEQ ID NO:1 and a peptide comprising, consisting essentially of, or consisting of the amino acid sequence SEQ ID NO:4; (d) a peptide comprising, consisting essentially of, or consisting of the amino acid sequence SEQ ID NO:2 and a peptide comprising, consisting essentially of, or consisting of the amino acid sequence SEQ ID NO:3; (e) a peptide comprising, consisting essentially of, or consisting of the amino acid sequence SEQ ID NO:2 and a peptide comprising, consisting essentially of, or consisting of the amino acid sequence SEQ ID NO:4; or (f) a peptide comprising, consisting essentially of, or consisting of the amino acid sequence SEQ ID NO:3 and a peptide comprising, consisting essentially of, or consisting of the amino acid sequence SEQ ID NO:4.

In some embodiments, an expression cassette encodes only three of the disclosed peptides; e.g., (a) a peptide comprising, consisting essentially of, or consisting of the amino acid sequence SEQ ID NO:1, a peptide comprising, consisting essentially of, or consisting of the amino acid sequence SEQ ID NO:2, and a peptide comprising, consisting essentially of, or consisting of the amino acid sequence SEQ ID NO:3; (b) a peptide comprising, consisting essentially of, or consisting of the amino acid sequence SEQ ID NO:1, a peptide comprising, consisting essentially of, or consisting of the amino acid sequence SEQ ID NO:2, and a peptide comprising, consisting essentially of, or consisting of the amino acid sequence SEQ ID NO:4; (c) a peptide comprising, consisting essentially of, or consisting of the amino acid sequence SEQ ID NO:2, a peptide comprising, consisting essentially of, or consisting of the amino acid sequence SEQ ID NO:3, and a peptide comprising, consisting essentially of, or consisting of the amino acid sequence SEQ ID NO:4; or (d) a peptide comprising, consisting essentially of, or consisting of the amino acid sequence SEQ ID NO:1, a peptide comprising, consisting essentially of, or consisting of the amino acid sequence SEQ ID NO:3, and a peptide comprising, consisting essentially of, or consisting of the amino acid sequence SEQ ID NO:4.

In some embodiments, an expression cassette encodes all four of the disclosed peptides; i.e., a peptide comprising, consisting essentially of, or consisting of the amino acid sequence SEQ ID NO:1, a peptide comprising, consisting essentially of, or consisting of the amino acid sequence SEQ ID NO:2, a peptide comprising, consisting essentially of, or consisting of the amino acid sequence SEQ ID NO:3, and a peptide comprising, consisting essentially of, or consisting of the amino acid sequence SEQ ID NO:4.

Therapeutic Uses

The disclosed peptides have a number of therapeutic applications and can be administered for a variety of purposes to both human and veterinary subjects. "Administer" as used herein includes direct administration of the disclosed peptides or modified versions thereof as well as indirect administration, e.g., using a nucleic acid molecule encoding the peptides or modified versions of the peptides, as described below. In some embodiments, administration is carried out in conjunction with one or more other therapeutic moieties. "In conjunction with" includes administration together with, before, or after administration of the one or more other therapeutic moieties.

Treatment of Hyperproliferative Disorders, Including Cancer

In some embodiments, one or more of the disclosed peptides or modified versions thereof can be administered to inhibit the progression of a hyperproliferative disorder, such as cancer. Such inhibition may include, for example, reducing proliferation of neoplastic or pre-neoplastic cells; destroying neoplastic or pre-neoplastic cells; and inhibiting metastasis or decreasing the size of a tumor.

Examples of cancers that can be treated using one or more of the disclosed peptides or modified versions thereof include, but are not limited to, melanomas, lymphomas, sarcomas, and cancers of the colon, kidney, stomach, bladder, brain (e.g., gliomas, glioblastomas, astrocytomas, medulloblastomas), prostate, bladder, rectum, esophagus, pancreas, liver, lung, breast, uterus, cervix, ovary, blood (e.g., acute myeloid leukemia, acute lymphoid leukemia, chronic myeloid leukemia, chronic lymphocytic leukemia, Burkitt's lymphoma, EBV-induced B-cell lymphoma).

Combination Cancer Therapies

In some embodiments, one or more of the disclosed peptides or modified versions thereof can be administered in conjunction with one or more therapies or immunotherapies, such as those described below.

In some embodiments, the second therapy comprises a second agent that reduces or blocks the activity of PD-1 (e.g., nivolumab, pembrolizumab, durvalumab) or In some embodiments, the second therapy comprises an agent that reduces or blocks the activity of PD-L1 (e.g., atezolizumab).

In some embodiments, the second therapy comprises an agent that reduces or blocks the activity of other inhibitory checkpoint molecules and/or molecules that suppress the immune system. These molecules include, but are not limited to:
1. Lymphocyte-activation gene-3 (LAG-3; see He et al., 2016; Triebel et al., 1990);
2. cytotoxic T-lymphocyte—associated antigen 4 (CTLA-4);
3. V-domain Immunoglobulin Suppressor of T cell Activation (VISTA, also known as c10orf54, PD-1H, DD1α, Gi24, Dies1, and SISP1; see US 2017/0334990, US 2017/0112929, Gao et al., 2017, Wang et al., 2011; Liu et al., 2015);
4. T-cell Immunoglobulin domain and Mucin domain 3 (TIM-3; see US 2017/0198041, US 2017/0029485, US 2014/0348842, Sakuishi et al., 2010);
5. killer immunoglobulin-like receptors (KIRs; see US 2015/0290316);
6. agents that inhibit indoleamine (2,3)-dioxygenase (IDO; see Mellemgaard et al., 2017);
7. B and T Lymphocyte Attenuator (BTLA; see US 2016/09222114); and
8. A2A adenosine receptor (A2AR; see Beavis et al., 2015; US 2013/0267515; US 2017/0166878; Leone et al., 2015; Mediavilla-Varela et al., 2017; Young et al., 2016).

Agents that reduce or block the activity of LAG-3 include, but are not limited to, BMS-986016, IMP321, and GSK2831781 (He et al., 2016).

Agents that reduce or block the activity of CTLA-4 include, but are not limited to, ipilimumab and tremelimumab.

Agents that reduce or block the activity of VISTA include, but are not limited to, small molecules, such as CA-170, and antibodies (e.g., Le Mercier et al., 2014).

Agents that reduce or block the activity of TIM-3 include, but are not limited to, antibodies such as MBG453 and TSR-022; see Dempke et al., 2017.

Agents that reduce or block the activity of KIRs include, but are not limited to, monoclonal antibodies such as IPH2101 and Lirilumab (BMS-986015, formerly IPH2102); see Benson & Caligiuri, 2014.

Agents that reduce or block the activity of IDO include, but are not limited to, epacadostat and agents disclosed in US 2017/0037125.

Agents that reduce or block the activity of BTLA include, but are not limited to, peptides (e.g., Spodzieja et al., 2017).

Agents that reduce or block the activity of A2AR include, but are not limited to, small molecules such as CPI-444 and vipadenant.

In some embodiments, the second therapy comprises a cytokine (e.g., interleukin 7).

In some embodiments, the second therapy comprises an agonist of a stimulatory checkpoint molecule. These molecules include, but are not limited to:
1. CD40;
2. OX40;
3. glucocorticoid-induced tumor necrosis factor-related protein (GITR); and
4. Inducible T-cell COStimulator (ICOS).

Agonists of CD40 include, but are not limited to, CD40 agonist monoclonal antibodies such as cp-870,893, Chi-Lob7/4, dacetuzumab, and lucatumumab. See, e.g., Vonderheide et al., 2007; Khubchandani et al., 2009; Johnson et al., 2010; Bensinger et al., 2012; Vonderheide and Glennie, 2013; Johnson et al., 2015.

Agonists of OX40 include, but are not limited to, OX40 agonist antibodies such as MOXR0916, MED16469, MED10562, PF-045618600, GSK3174998, and INCCAGN01949, and OX40L-Fc fusion proteins, such as MEDI6383. See, e.g., Huseni et al., 2014; Linch et al., 2015; Messenheimer et al., 2017. See also Shrimali et al., 2017.

Agonists of GITR include, but are not limited to, MEDI1873. See, e.g., Schaer et al., 2012; Tigue et al., 2017.

Agonists of ICOS include, but are not limited to, ICOS agonist antibodies JTX-2011 and GSK3359609. See, e.g., Harvey et al., 2015; Michaelson et al., 2016.

In other embodiments, the second therapy comprises a 4-1BB agonist (Shindo et al., 2015), such as urelumab; a 4-1BB antagonist (see US 2017/0174773); an inhibitor of anaplastic lymphoma kinase (ALK; Wang et al., 2014; US 2017/0274074), such as crizotinib, ceritinib, alectinib, PF-06463922, NVP-TAE684, AP26113, TSR-011, X-396, CEP-37440, RXDX-101; an inhibitor of histone deacetylase (HDAC; see US 2017/0327582); a VEGFR inhibitor, such as axitinib, sunitinib, sorafenib, tivozanib, bevacizumab; and/or an anti-CD27 antibody, such as varlilumab.

In some embodiments, the second therapy comprises a cancer vaccine (e.g., Duraiswamy et al., 2013). A "cancer vaccine" is an immunogenic composition intended to elicit an immune response against a particular antigen in the individual to which the cancer vaccine is administered. A cancer vaccine typically contains a tumor antigen which is able to induce or stimulate an immune response against the tumor antigen. A "tumor antigen" is an antigen that is present on the surface of a target tumor. A tumor antigen may be a molecule which is not expressed by a non-tumor cell or may be, for example, an altered version of a molecule expressed by a non-tumor cell (e.g., a protein that is misfolded, truncated, or otherwise mutated).

In some embodiments, the second therapy comprises a chimeric antigen receptor (CAR) T cell therapy. See, e.g., John et al., 2013; Chong et al., 2016.

Additional Therapeutic Uses

In some embodiments, one or more of the disclosed peptides or modified versions thereof can be administered to treat infectious diseases, including chronic infections, caused, e.g., by viruses, fungi, bacteria, and protozoa, and helminths.

Examples of viral agents include human immunodeficiency virus (HIV), Epstein Barr Virus (EBV), Herpes simplex (HSV, including HSV1 and HSV2), Human Papillomavirus (HPV), Varicella zoster (VSV) Cytomegalovirus (CMV), and hepatitis A, B, and C viruses.

Examples of fungal agents include *Aspergillus, Candida, Coccidioides, Cryptococcus*, and *Histoplasma capsulatum.*

Examples of bacterial agents include Streptococcal bacteria (e.g., *pyogenes, agalactiae, pneumoniae*), *Chlamydia pneumoniae, Listeria monocytogenes*, and *Mycobacterium tuberculosis.*

Examples of protozoa include *Sarcodina* (e.g., *Entamoeba*), *Mastigophora* (e.g., *Giardia*), *Ciliophora* (e.g., *Balantidium*), and *Sporozoa* (e.g., *Plasmodium falciparum, Cryptosporidium*).

Examples of helminths include *Platyhelminths* (e.g., trematodes, cestodes), *Acanthocephalins*, and *Nematodes.*

In some embodiments one or more of the disclosed peptides or modified versions thereof can be administered as a vaccine adjuvant in conjunction with a vaccine to enhance a response to vaccination (e.g., by increasing effector T cells and/or reducing T cell exhaustion). The vaccine can be, for example, an RNA vaccine (e.g., US 2016/0130345, US 2017/0182150), a DNA vaccine, a recombinant vector, a protein vaccine, or a peptide vaccine. Such vaccines can be delivered, for example, using virus-like particles, as is well known in the art.

In some embodiments one or more of the disclosed peptides or modified versions thereof can be administered to treat sepsis.

In some embodiments one or more of the disclosed peptides or modified versions thereof can be administered to promote hair color re-pigmentation. In some embodiments one or more of the disclosed peptides or modified versions thereof can be administered to promote lightening of pigmented skin lesions.

Administration of Peptides

In some embodiments, one or more of the disclosed peptides themselves, or modified versions thereof, are administered. In some of these embodiments, a peptide carrier system is used. A number of peptide carrier systems are known in the art, including microparticles, polymeric nanoparticles, liposomes, solid lipid nanoparticles, hydrophilic mucoadhesive polymers, thiolated polymers, polymer matrices, nanoemulsions, and hydrogels. See Patel et al. (2014), Bruno et al. (2013), Feridooni et al. (2016). Any suitable system can be used.

In some embodiments, engineered T cell-based therapies that express and secrete a peptide or protein can be used to deliver PD-1 inhibition at the site of engagement of the T cell receptor with an antigen. The T cell-based therapy could be, for example, a CAR-T cell that expresses one or more of the disclosed peptides or modified versions thereof. Either inducible or constitutive expression can be used.

In other embodiments one or more of the disclosed peptides or modified versions thereof are delivered using one or more nucleic acids encoding the peptide(s) (e.g., DNA, cDNA, PNA, RNA or a combination thereof); See, e.g., US 2017/0165335. Nucleic acids encoding one or more peptides can be delivered using a variety of delivery systems known in the art. Nucleic acid delivery systems include, but are not limited to, gene-gun; cationic lipids and cationic polymers; encapsulation in liposomes, microparticles, or microcapsules; electroporation; virus-based, and bacterial-based delivery systems. Virus-based systems include, but are not limited to, modified viruses such as adenovirus, adeno-associated virus, herpes virus, retroviruses, vaccinia virus, or hybrid viruses containing elements of one or more viruses. US 2002/0111323 describes use of "naked DNA," i.e., a "non-infectious, non-immunogenic, non-integrating DNA sequence," free from "transfection-facilitating proteins, viral particles, liposomal formulations, charged lipids and calcium phosphate precipitating agents," to administer a peptide. Bacterial-based delivery systems are disclosed, e.g., in Van Dessel et al. (2015) and Yang et al. (2007).

In some embodiments, a peptide is administered via an RNA molecule encoding the peptide. In some embodiments, the RNA molecule is encapsulated in a nanoparticle. In some embodiments, the nanoparticle comprises a cationic polymer (e.g., poly-L-lysine, polyamidoamine, polyethyleneimine, chitosan, poly(β-amino esters). In some embodiments, the nanoparticle comprises a cationic lipid or an ionizable lipid. In some embodiments, the RNA molecule is conjugated to a bioactive ligand (e.g., N-acetylgalactosamine (GalNAc), cholesterol, vitamin E, antibodies, cell-penetrating peptides). See, e.g., Akinc et al. (2008), Akinc et al. (2009), Anderson et al. (2003), Behr (1997), Boussif et al. (1995), Chen et al. (2012), Dahlman et al. (2014), Desigaux et al. (2007), Dong et al. (2014), Dosta et al. (2015), Fenton et al. (2016), Guo et al. (2012), Howard et al. (2006), Kaczmarek et al. (2016), Kanasty et al. (2013), Kauffman et al. (2015), Kozielski et al. (2013), Leus et al. (2014), Lorenz et al. (2004), Love et al. (2010), Lynn & Langer (2000), Moschos et al. (2007), Nair et al. (2014), Nishina et al. (2008), Pack et al. (2005), Rehman et al. (2013), Schroeder et al. (2010), Tsutsumi et al. (2007), Tzeng et al. (2012), Won et al. (2009), Xia et al. (2009), Yu et al. (2016).

In some embodiments, an RNA molecule can be modified to reduce its chances of degradation or recognition by the immune system. The ribose sugar, the phosphate linkage, and/or individual bases can be modified. See, e.g., Behlke (2008), Bramsen (2009), Chiu (2003), Judge & MacLachlan (2008), Kauffman (2016), Li (2016), Morrissey (2005), Prakash (2005), Pratt & MacRae (2009), Sahin (2014), Soutschek (2004), Wittrup & Lieberman (2015). In some embodiments, the modification is one or more of a ribo-difluorotoluyl nucleotide, a 4'-thio modified RNA, a boranophosphate linkage, a phosphorothioate linkage, a 2'-O-methyl (2'-OMe) sugar substitution, a 2'-fluoro (2'-F), a 2'-O-methoxyethyl (2'-MOE) sugar substitution, a locked nucleic acid (LNA), and an L-RNA.

Routes of Administration, Pharmaceutical Compositions, and Devices

Pharmaceutical compositions comprising an effective amount of any of the active agents described in the paragraphs above include a pharmaceutically acceptable vehicle. The "pharmaceutically acceptable vehicle" may comprise one or more substances which do not affect the biological activity of the active agent(s) and, when administered to a patient, does not cause an adverse reaction. Pharmaceutical compositions may be liquid or may be lyophilized. Lyophilized compositions may be provided in a kit with a suitable liquid, typically water for injection (WFI) for use in reconstituting the composition. Other suitable forms of pharmaceutical compositions include suspensions, emulsions, and tablets.

Routes of administration include injection or infusion (e.g., epidural, intradermal, intramuscular, intraperitoneal, intravenous, sub-cutaneous), transdermal (e.g., US 2017/0281672), mucosal (e.g., intranasal or oral), pulmonary, and topical (e.g., US 2017/0274010) administration. See, e.g., US 2017/0101474.

Administration can be systemic or local. In addition to local infusions and injections, implants can be used to achieve a local administration. Examples of suitable materials include, but are not limited to, sialastic membranes, polymers, fibrous matrices, and collagen matrices.

Topical administration can be by way of a cream, ointment, lotion, transdermal patch (such as a microneedle patch), or other suitable forms well known in the art.

Administration can also be by controlled release, for example, using a microneedle patch, pump and/or suitable polymeric materials. Examples of suitable materials include, but are not limited to, poly(2-hydroxy ethyl methacrylate), poly(methyl methacrylate), poly(acrylic acid), poly(ethylene-co-vinyl acetate), poly(methacrylic acid), polyglycolides (PLG), polyanhydrides, poly(N-vinyl pyrrolidone), poly(vinyl alcohol), polyacrylamide, poly(ethylene glycol), polylactides (PLA), poly(lactide-co-glycolides) (PLGA), and polyorthoesters.

Devices comprising any of the active agents described above include, but are not limited to, syringes, pumps, transdermal patches, spray devices, vaginal rings, and pessaries.

Example 1. Peptide Library Screening

The TriCo-20™ (TRICO-20™) and TriCo-16™ (TRICO-16™) Phage Display Peptide Libraries (Creative Biolabs, 45-1 Ramsey Road, Shirley, N.Y. 11967) were screened to identify binders of soluble recombinant human PD-1 receptor. After the fourth round of panning, obvious enrichment for specific binders was observed, and individual peptides were confirmed as weakly specific binders in a clonal phage ELISA. A fifth round of panning led to greater enrichment. Table 1 lists four peptides which showed strong specific binding in the clonal phage ELISA.

TABLE 1

| Clone | Clonal Phase ELISA coated signal | Clonal Phase ELISA uncoated signal | peptide sequence | SEQ ID NO: |
|---|---|---|---|---|
| QP20 | 0.851 | 0.446 | QTRTVPMPKIHHPPWQNVVP | 1 |
| HD20 | 0.281 | 0.109 | HHHQVYQVRSHWTGMHSGHD | 2 |
| WQ20 | 0.275 | 0.115 | WNLPASFHNHHIRPHEHEWIQ | 3 |
| SQ20 | 0.284 | 0.159 | SSYHHFKMPELHFGKNTFHQ | 4 |

Example 2. Competitive PD-1:PD-L1 Binding Inhibition Assay

Briefly, detection of cell surface PD-1 on Jurkat cells was accomplished by incubating cells with the human PD-L1-Fc fusion protein, followed by detection of the recombinant molecule with a fluorescently labeled anti-human Fc antibody. Flow cytometry was performed to detect binding between PD-1 and the PD-L1 recombinant protein. Quantitative binding measurement was then determined by mean fluorescence intensity (MFI).

Figure 2:
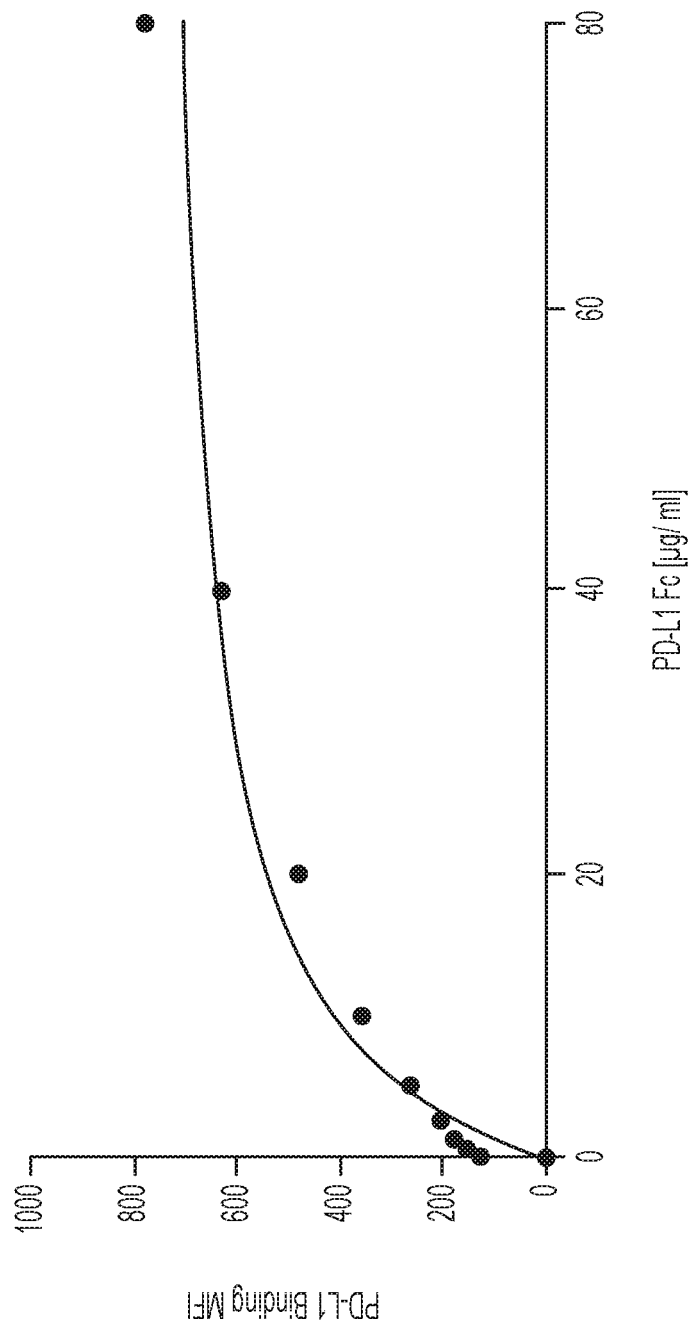
FIG. 2. Graph showing saturatable binding of PD-L1 Fc to Jurkat cells.
Figure 3A:
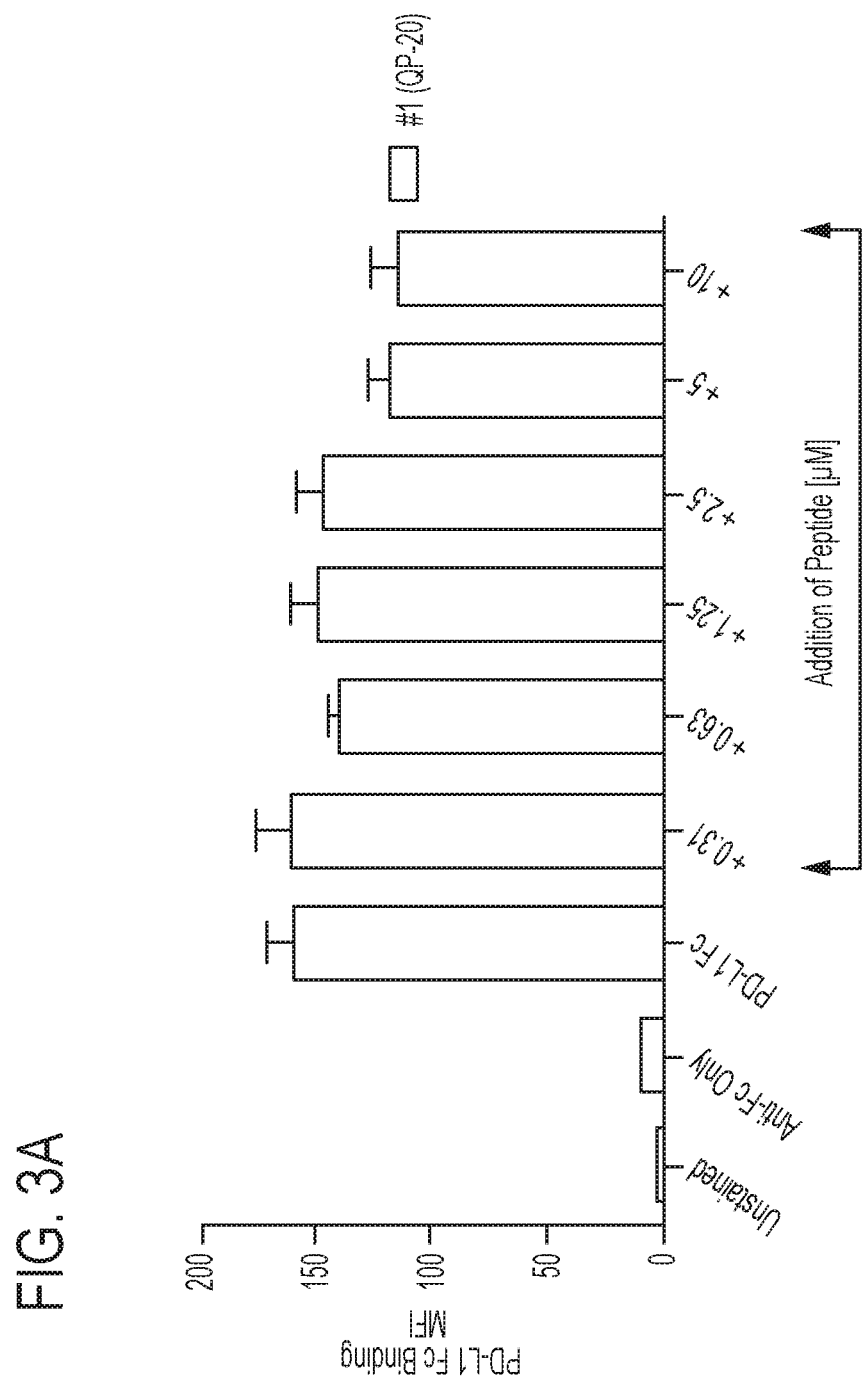
FIGS. 3A-B. Graphs showing effect of peptide QP20 on binding of PD-L1 to PD-1.
Figure 3B:
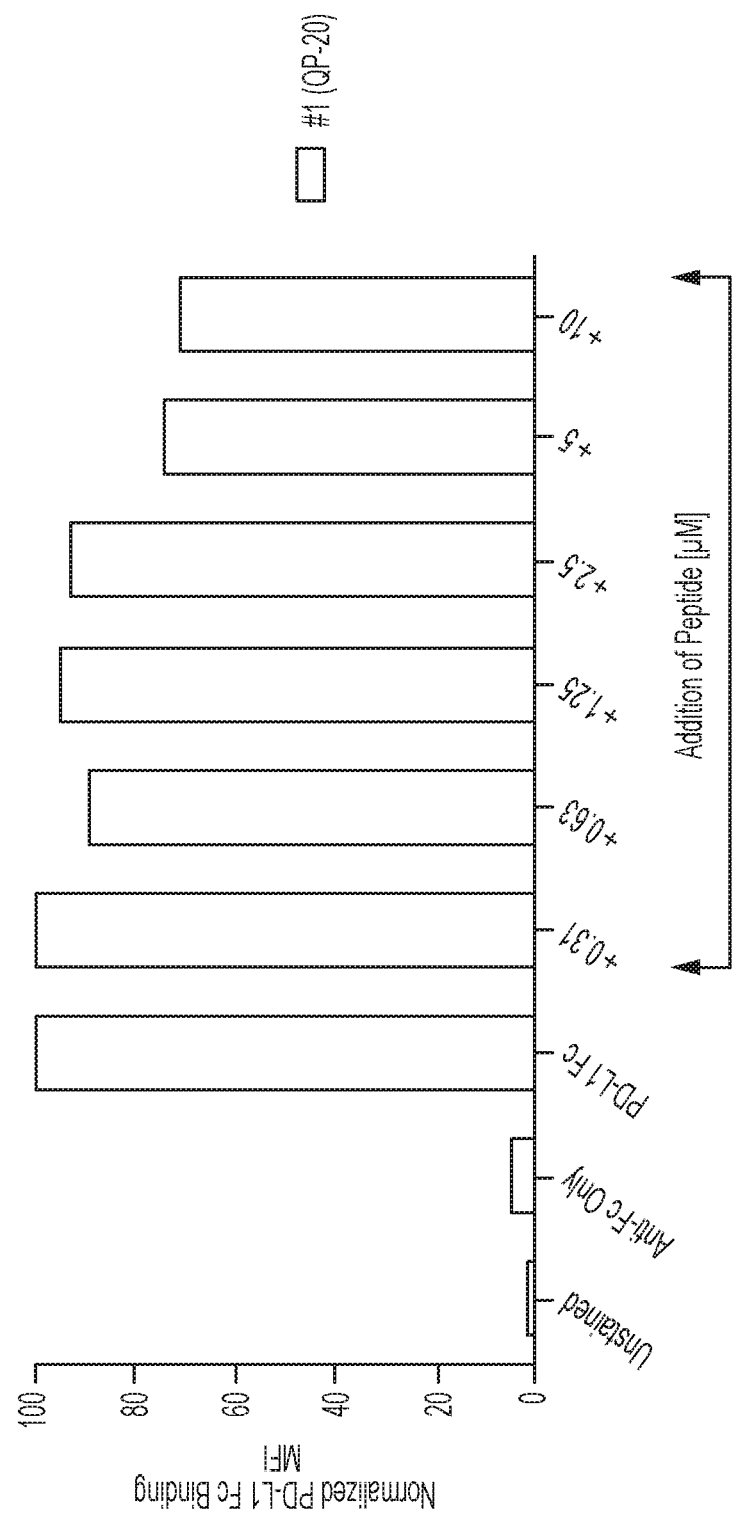
Figure 4B:
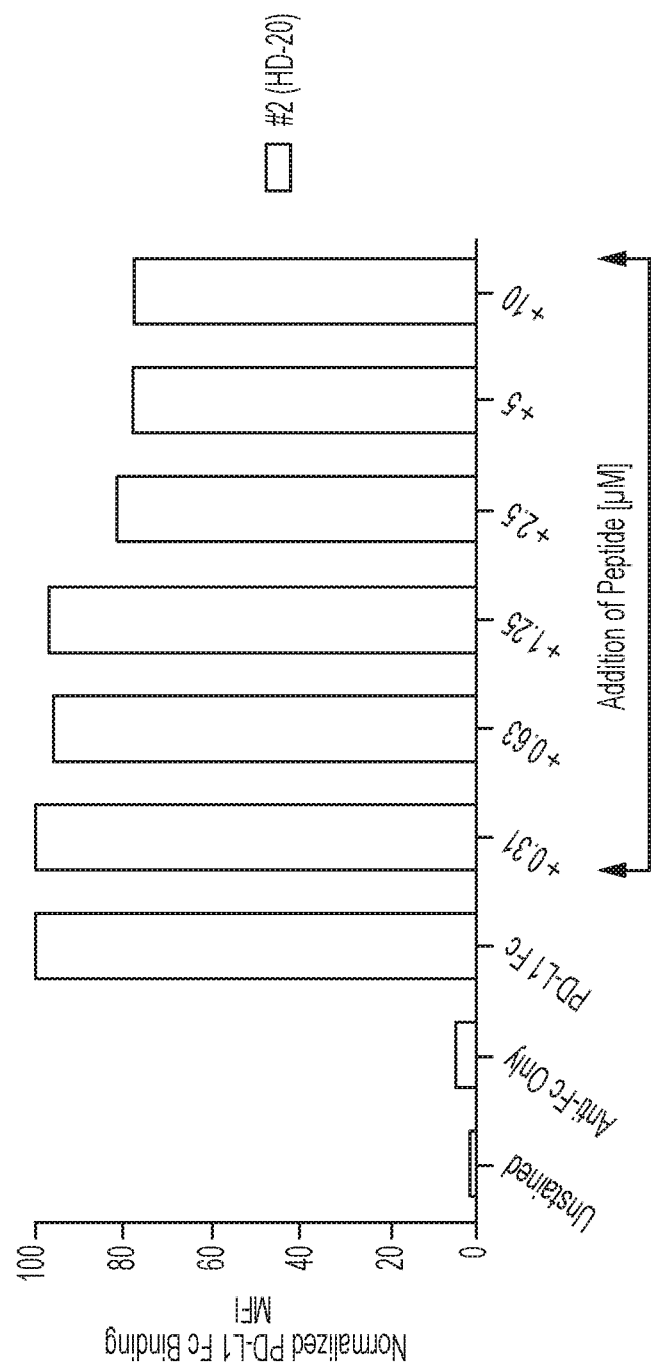
Figure 5A:
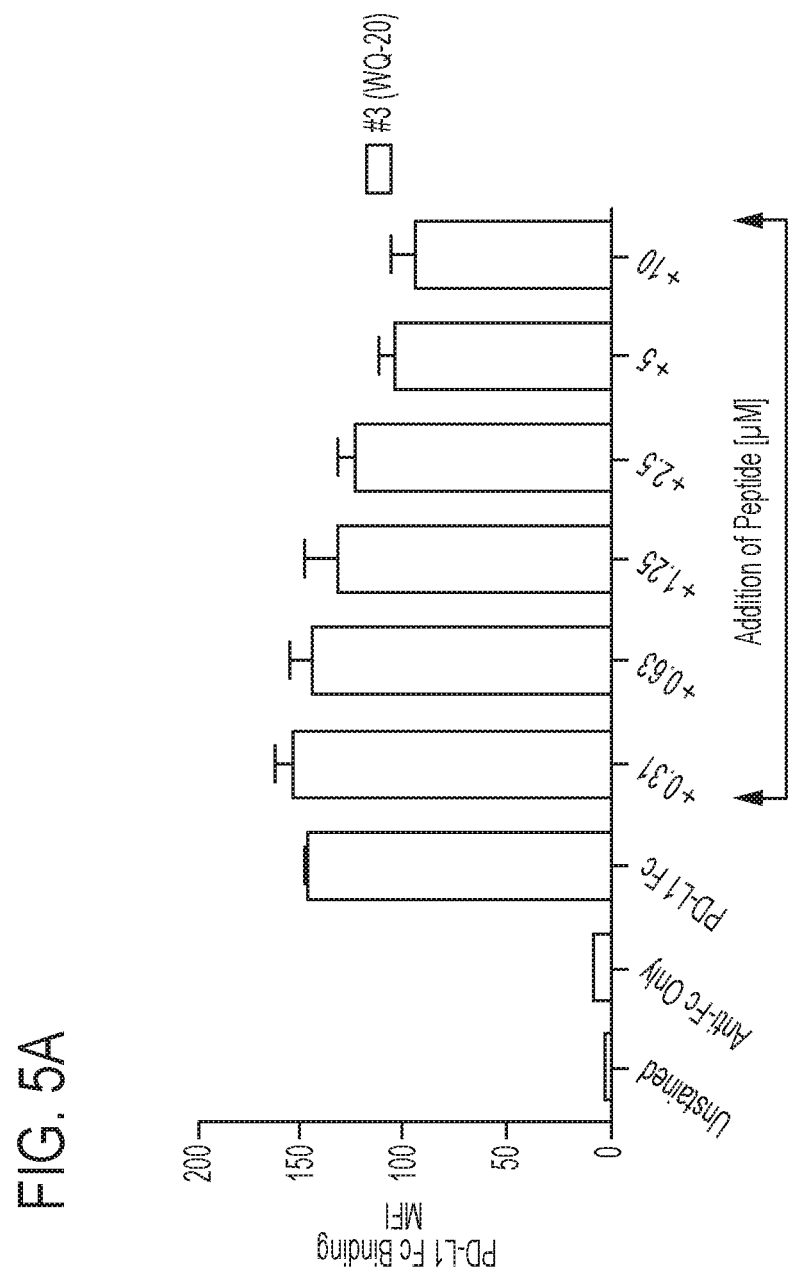
Figure 6A:
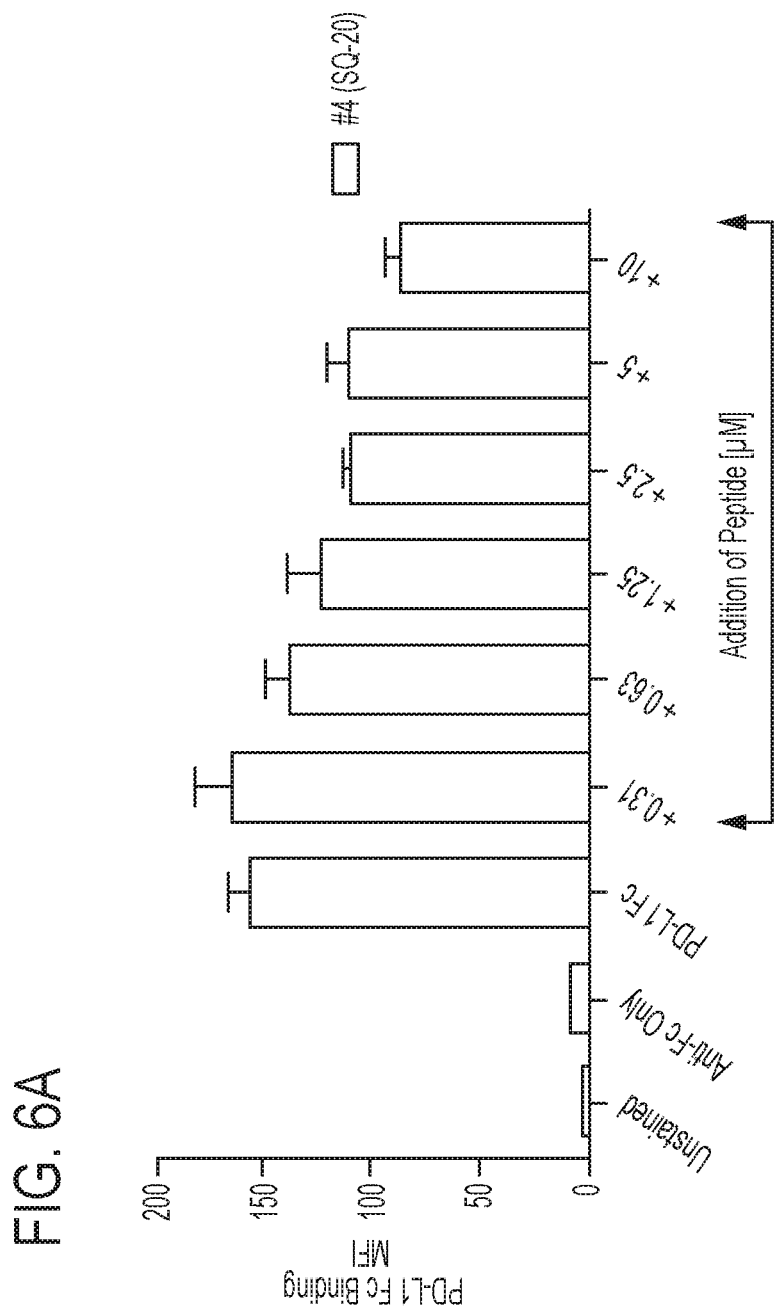
FIGS. 6A-B. Graphs showing effect of peptide SQ20 on binding of PD-L1 to PD-1.
Figure 6B:
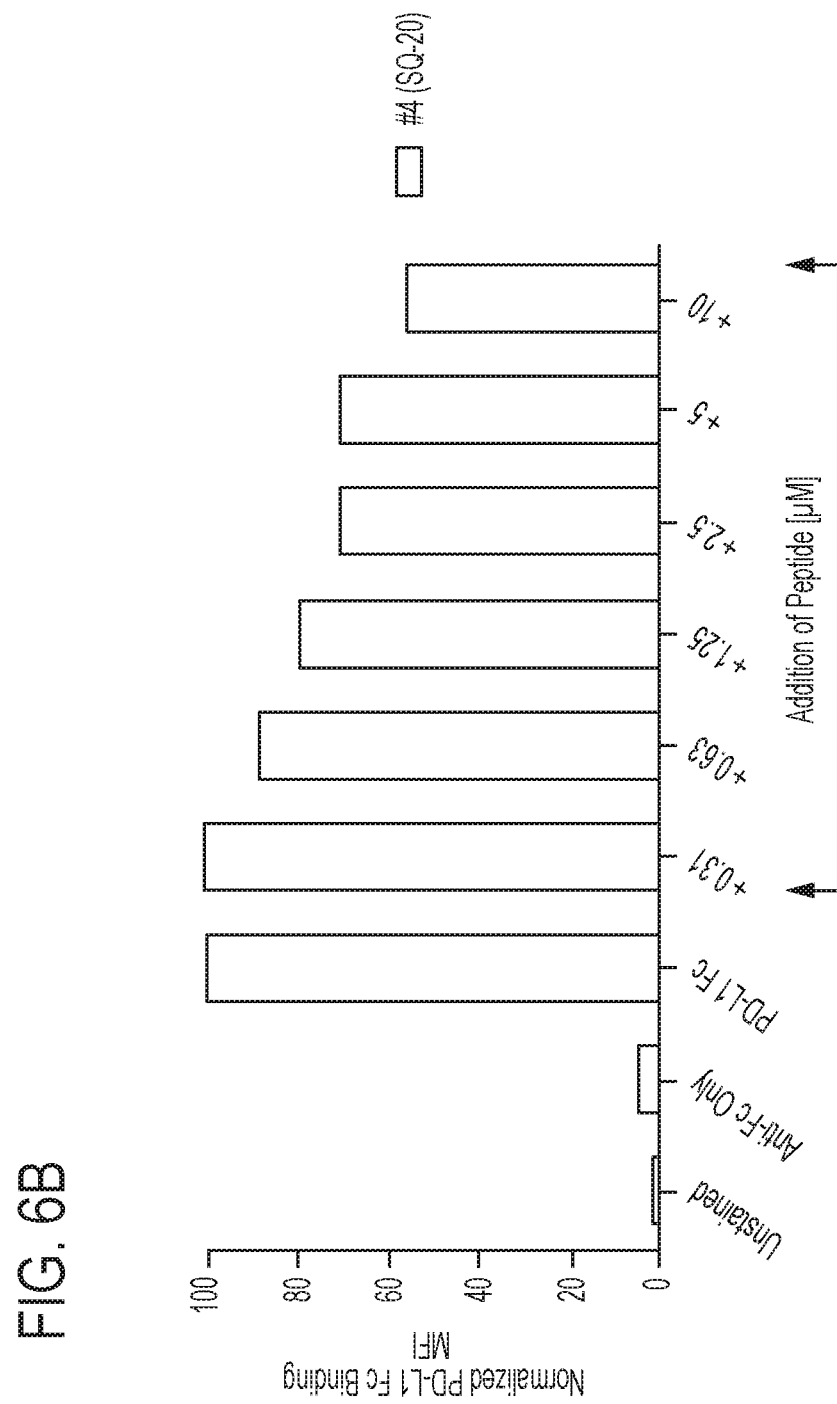

Jurkat Cell-surface expression of PD1 and binding of PD-L1 to these cells were verified as shown in FIGS. 1 and 2. The results are shown in FIGS. 3A-B, 4A-B, 5A-B, and 6A-B.

Example 3. Cell-Based Reporter Assay

A cell-based reporter assay was used to assess whether binding of the four peptides identified above was sufficient to block the interaction with PD-1 and its ligand PD-L1. The components of the assay include a Jurkat T cell line that stably expresses human PD-1 and a luciferase reporter, a CHO cell line that stably expressed human PD-L1, and a positive control anti-PD-1 antibody that blocks the interaction of PD-1 and PD-L1, resulting in a measurable effect in the assay. The luciferase reporter in the Jurkat T cell line is triggered by IL-1, NFAT, or NF-κB response elements in the promoter region. The Jurkat T cells are pre-treated with CD3 and immediately cryopreserved for use in the assay. Interaction of the Jurkat T cells with the PD-L1 expressing cell line inhibits the intracellular mechanism by which the luciferase construct is activated, thereby preventing luciferase expression. A molecule that binds to either PD-1 on the Jurkat T cells or to PD-L1 on the CHO cells sufficiently to prevent their interaction permits the Jurkat T cells to produce luciferase. CellTiter-Glo® (CELLTITER-GLO®, Promega) was used to measure luciferase expression.

Figure 7A:
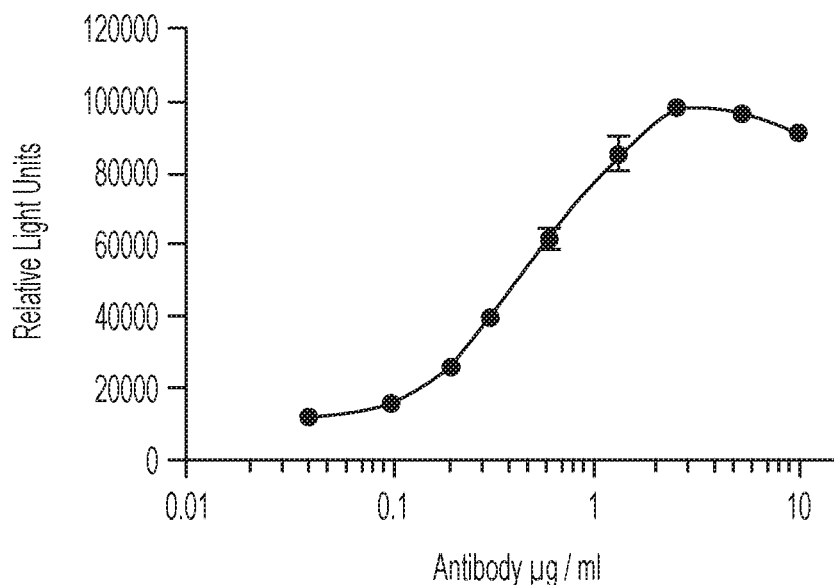
FIG. 7A. Graph showing the effect of an anti-human PD-1 antibody on the interaction between PD-1-expressing Jurkat T cells and PD-L1-expressing CHO cells that results in inhibition of a PD-1 mediated suppression of luciferase reporter that is under the control of promoter containing IL-2, NFAT, and NF-kB response elements.
Figure 7B:
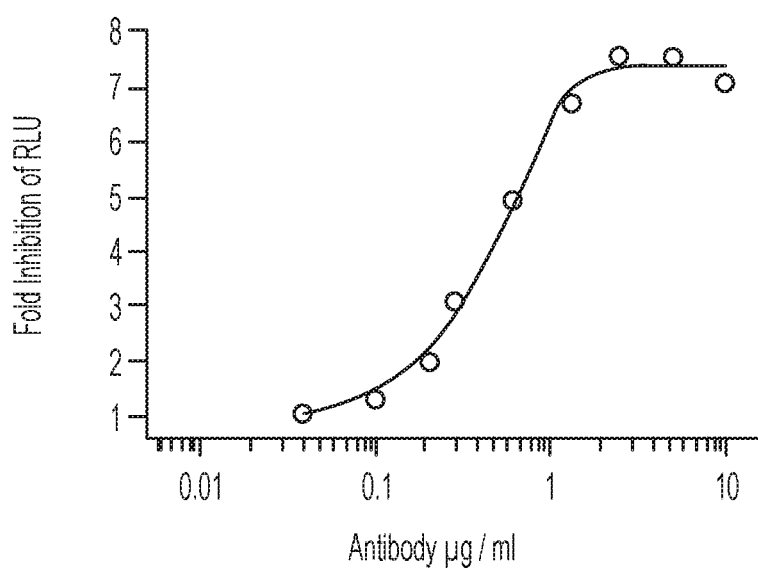
FIG. 7B. Graph showing the effect of an anti-human PD-1 antibody on the interaction between PD-1-expressing Jurkat T cells and PD-L1-expressing CHO cells (data in 7A expressed as fold inhibition).

The results of positive control assays using the anti-PD-1 control antibody are shown in FIGS. 7A-B. These results demonstrate that the control antibody restores luciferase expression in a dose-dependent manner, with peak-fold inhibition of approximately 8 at an antibody concentration of 20 µM.

Figure 8A:
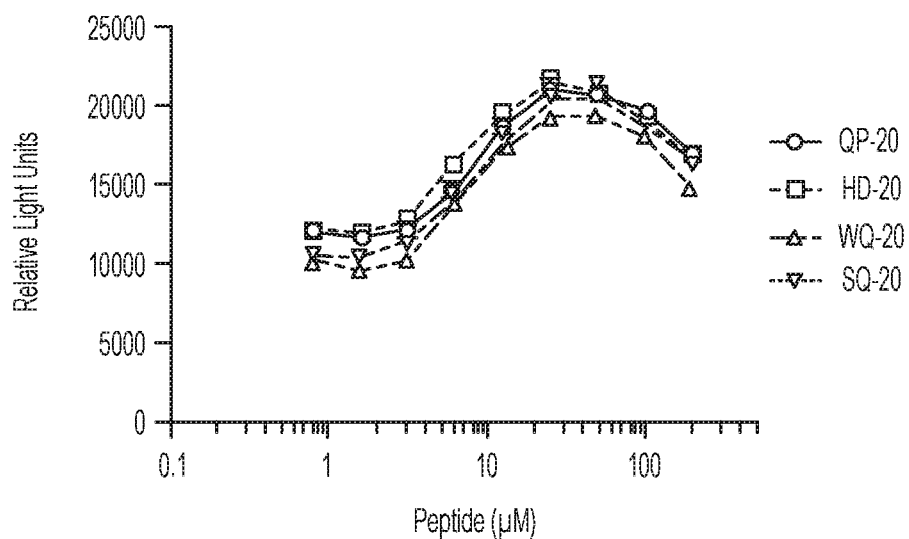
FIG. 8A. Graph showing that PD-1 peptide inhibitors inhibit, in a dose-dependent manner, the interaction between PD-1-expressing Jurkat T cells and PD-L1-expressing CHO cells, which results in increased luciferase reporter expression.
Figure 8B:
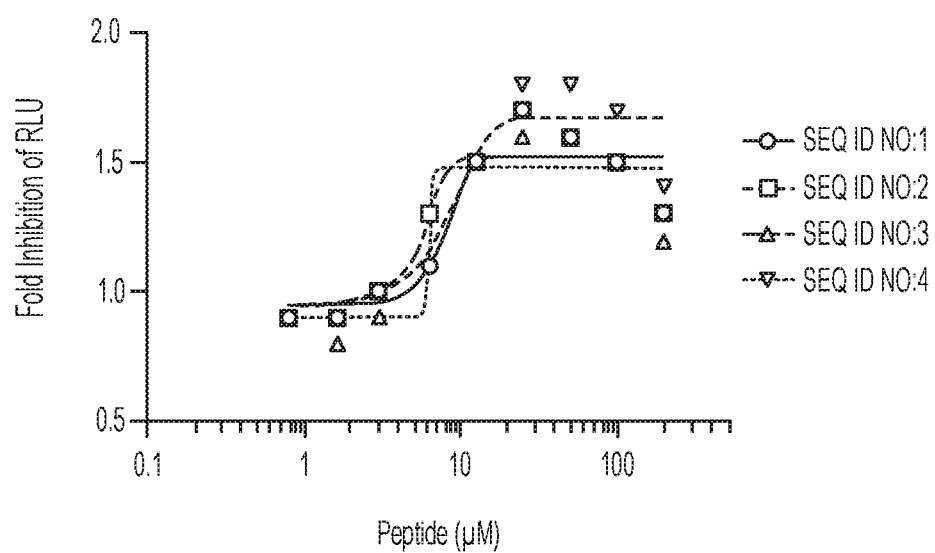
FIG. 8B. Graph showing the effect of an anti-human PD-1 antibody on the interaction between PD-1-expressing Jurkat T cells and PD-L1-expressing CHO cells (data in 8B expressed as fold inhibition).
Figure 9:
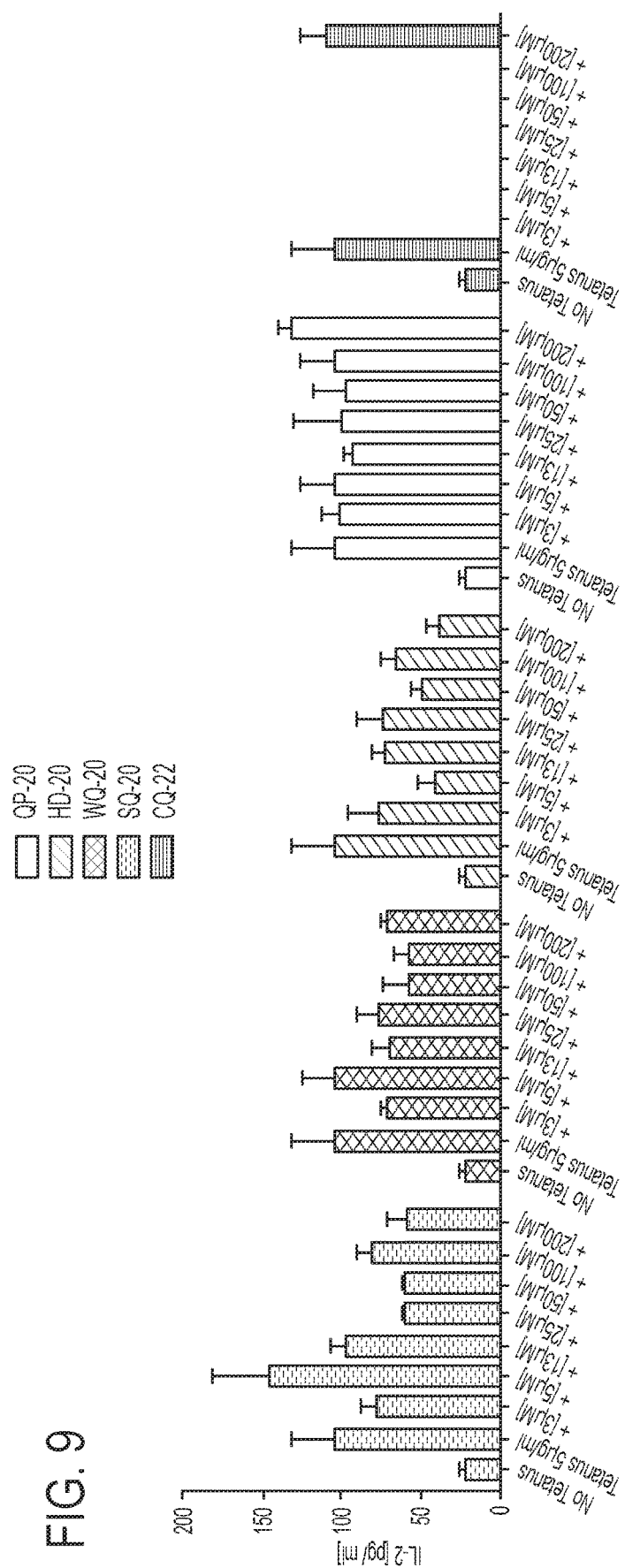
FIG. 9. Graph showing IL-2 production by peripheral blood mononuclear cells (PBMCs) in a tetanus toxoid recall assay after culture with peptides QP20, HD20, WQ20, SQ20, or CQ-22.
Figure 10:
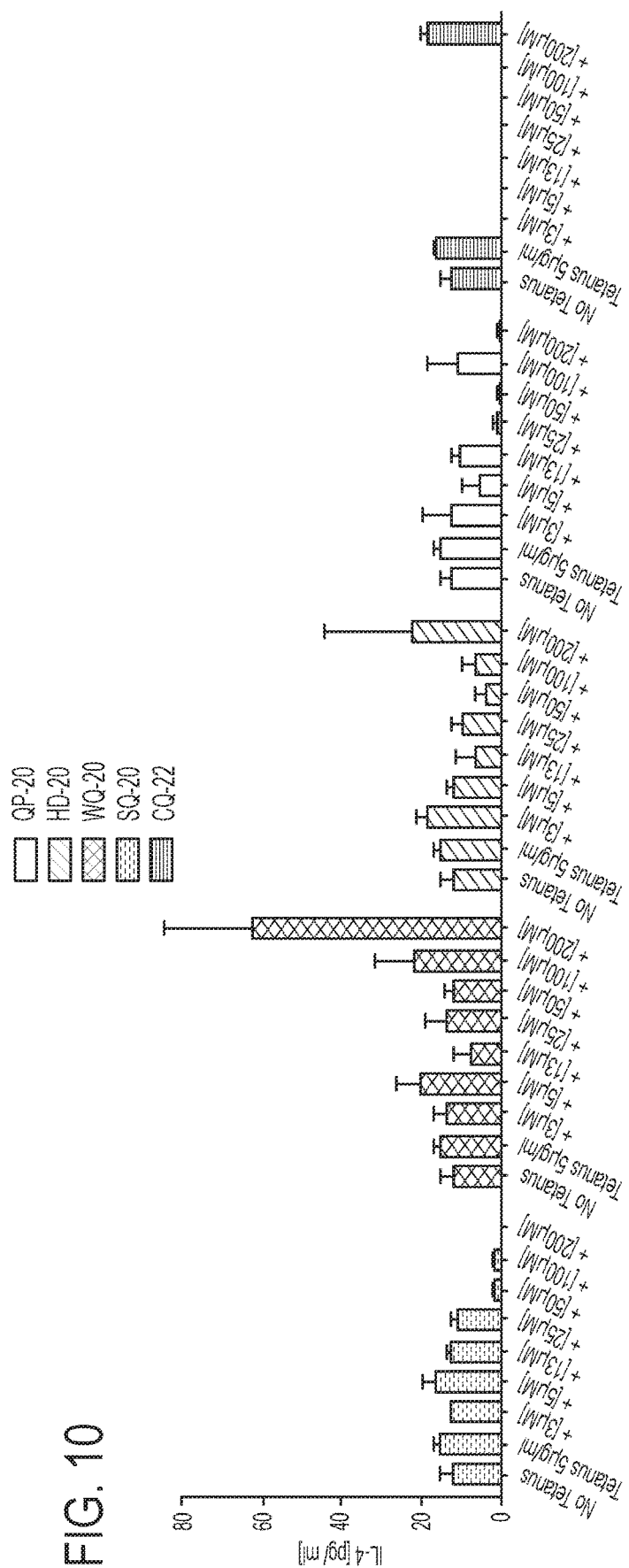
FIG. 10. Graph showing IL-4 production by PBMCs in a tetanus toxoid recall assay after culture with peptides QP20, HD20, WQ20, SQ20, or CQ-22.
Figure 11:
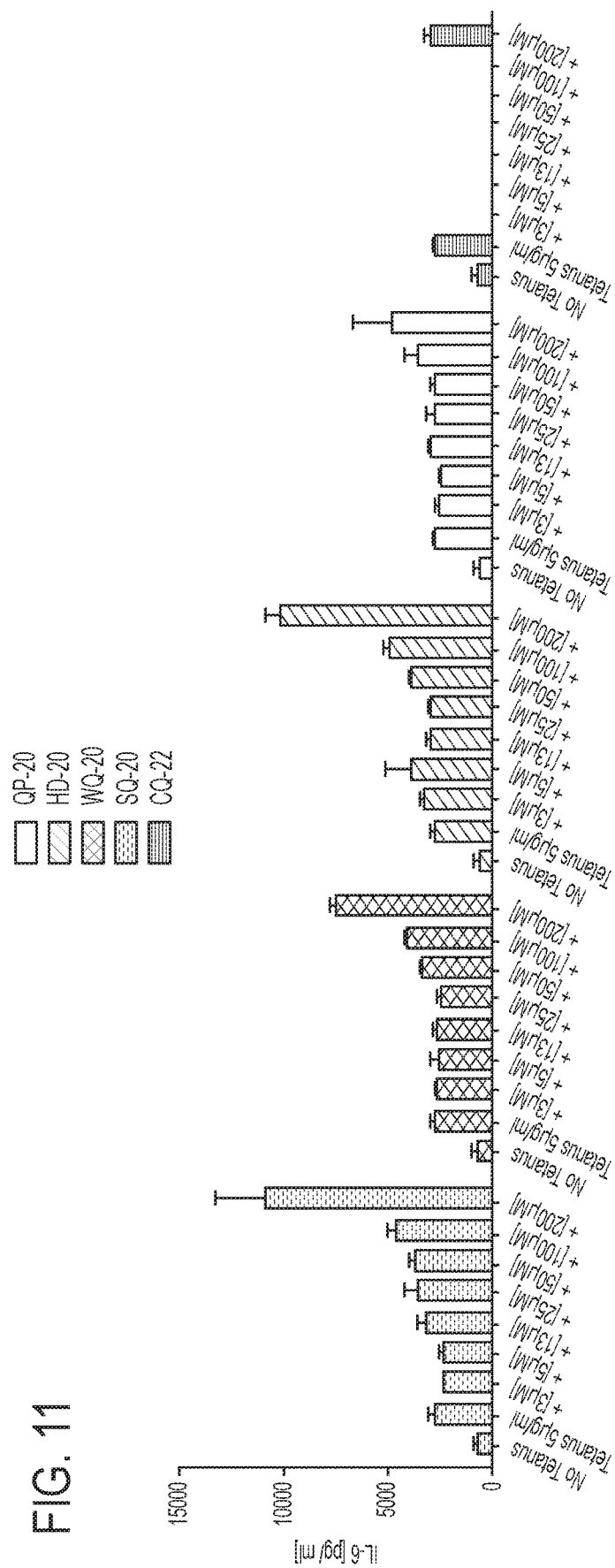
FIG. 11. Graph showing IL-6 production by PBMCs in a tetanus toxoid recall assay after culture with peptides QP20, HD20, WQ20, SQ20, or CQ-22.
Figure 12:
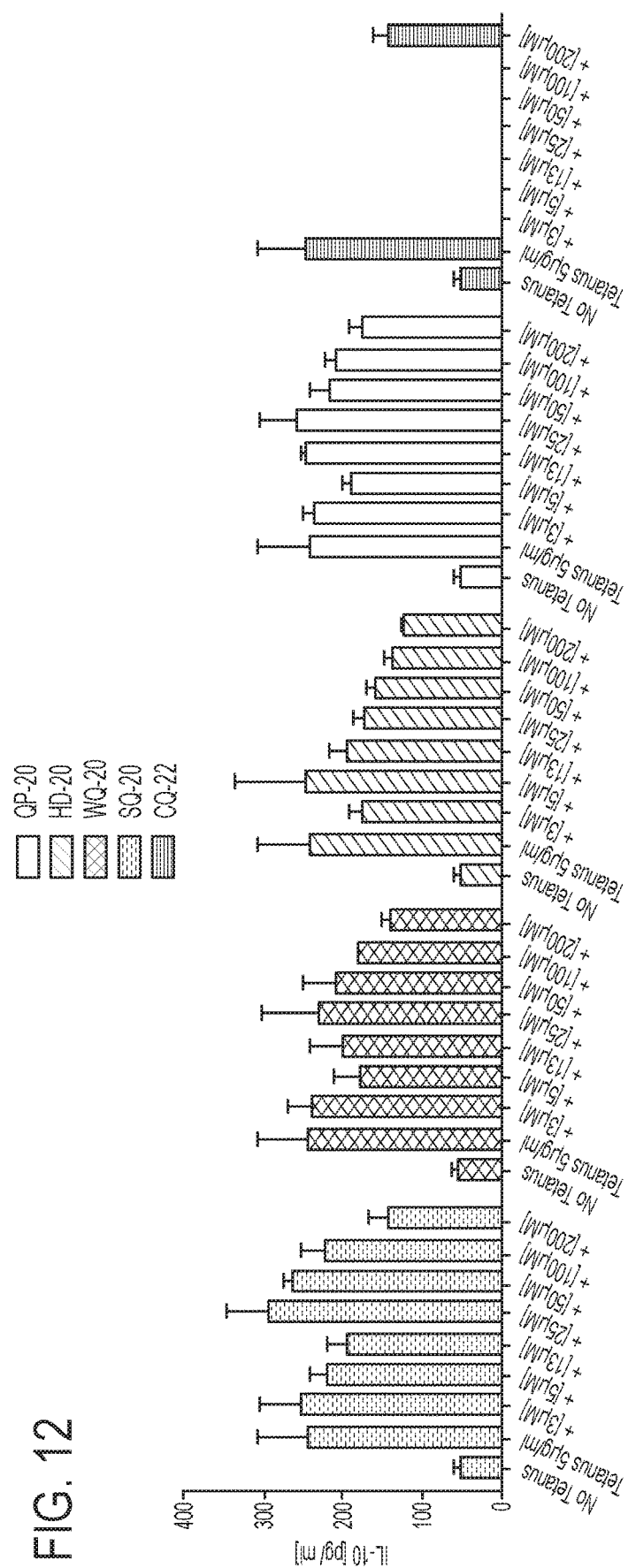
FIG. 12. Graph showing IL-10 production by PBMCs in a tetanus toxoid recall assay after culture with peptides QP20, HD20, WQ20, SQ20, or CQ-22.
Figure 13:
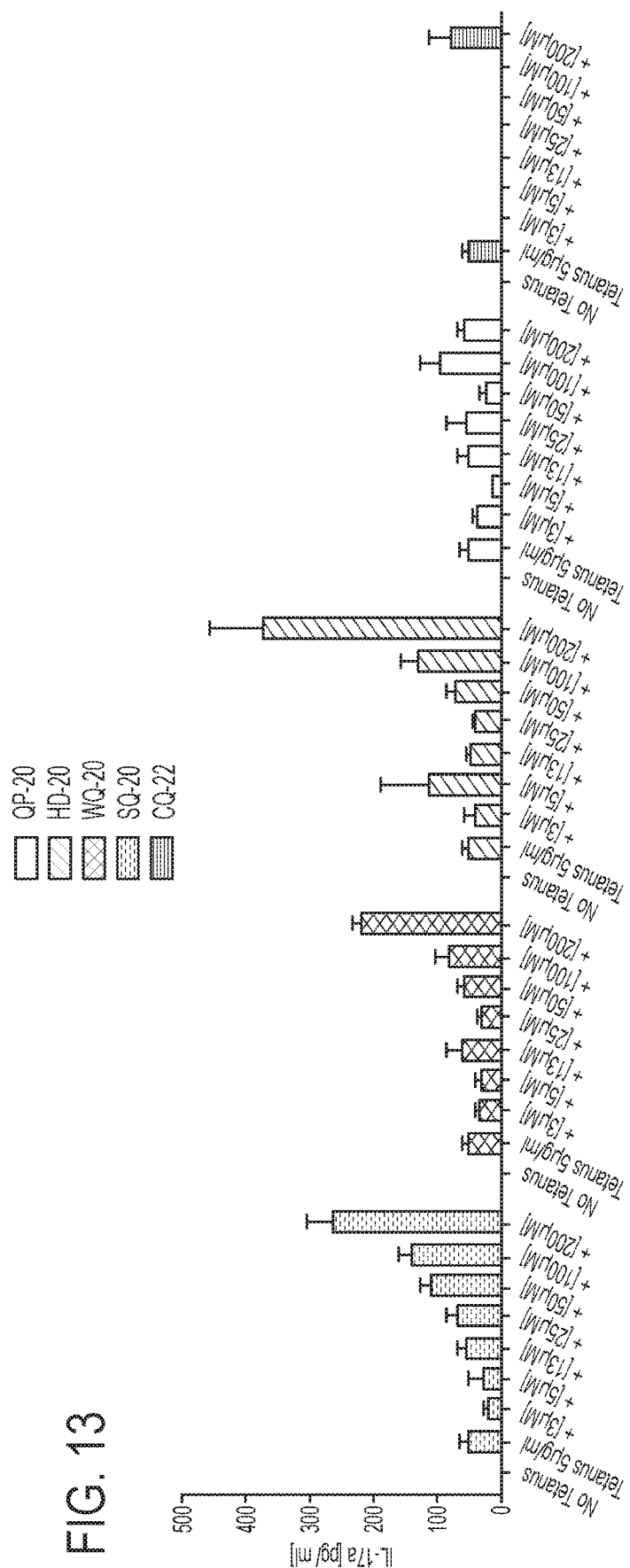
FIG. 13. Graph showing IL-17a production by PBMCs in a tetanus toxoid recall assay, after culture with peptides QP20, HD20, WQ20, SQ20, or CQ-22.
Figure 14:
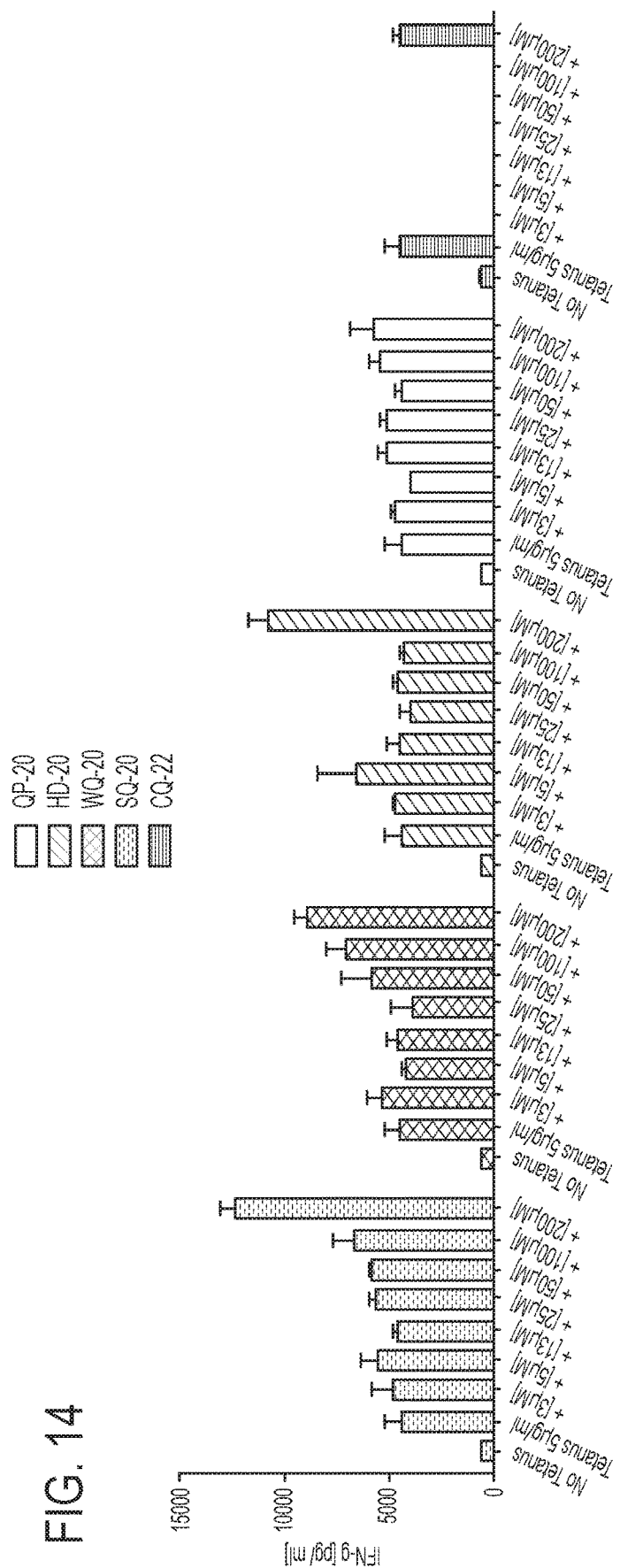
FIG. 14. Graph showing IFNγ production by PBMCs in a tetanus toxoid recall assay, after culture with peptides QP20, HD20, WQ20, SQ20, or CQ-22.
Figure 15:
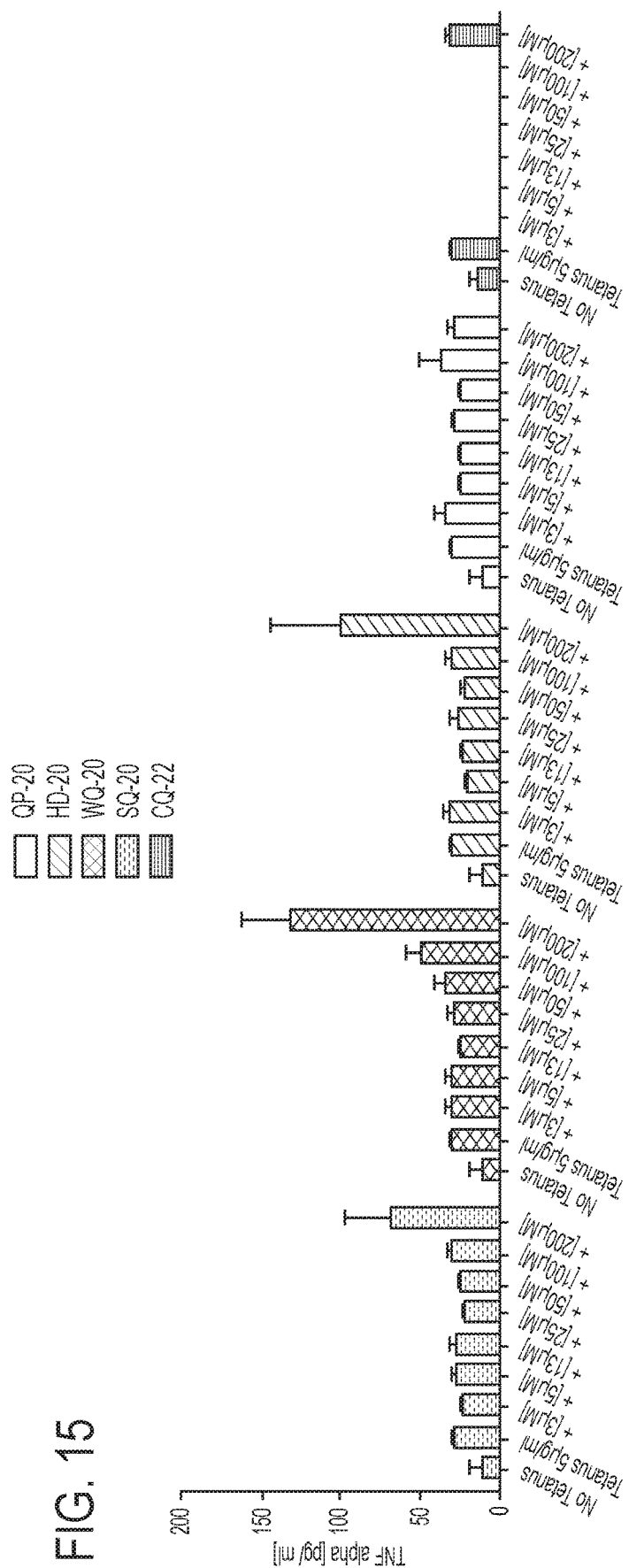
FIG. 15. Graph showing TNFα production by PBMCs in a tetanus toxoid recall assay, after culture with peptides QP20, HD20, WQ20, SQ20, or CQ-22.
Figure 16:
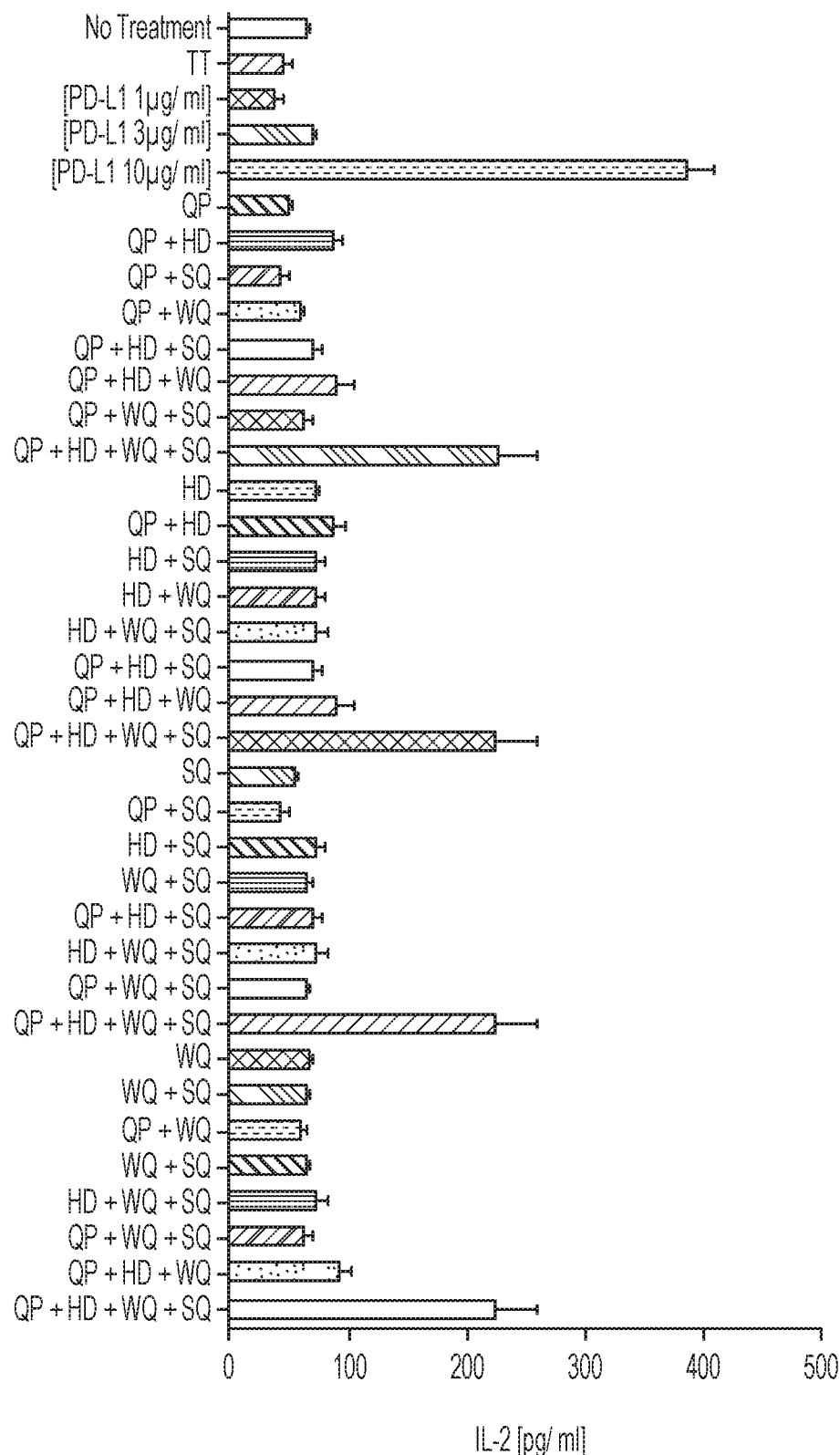
FIG. 16. Graph showing IL-2 production by PBMCs in a tetanus toxoid recall assay, after culture with various combinations of peptides QP20, HD20, WQ20, and SQ20.
Figure 17:
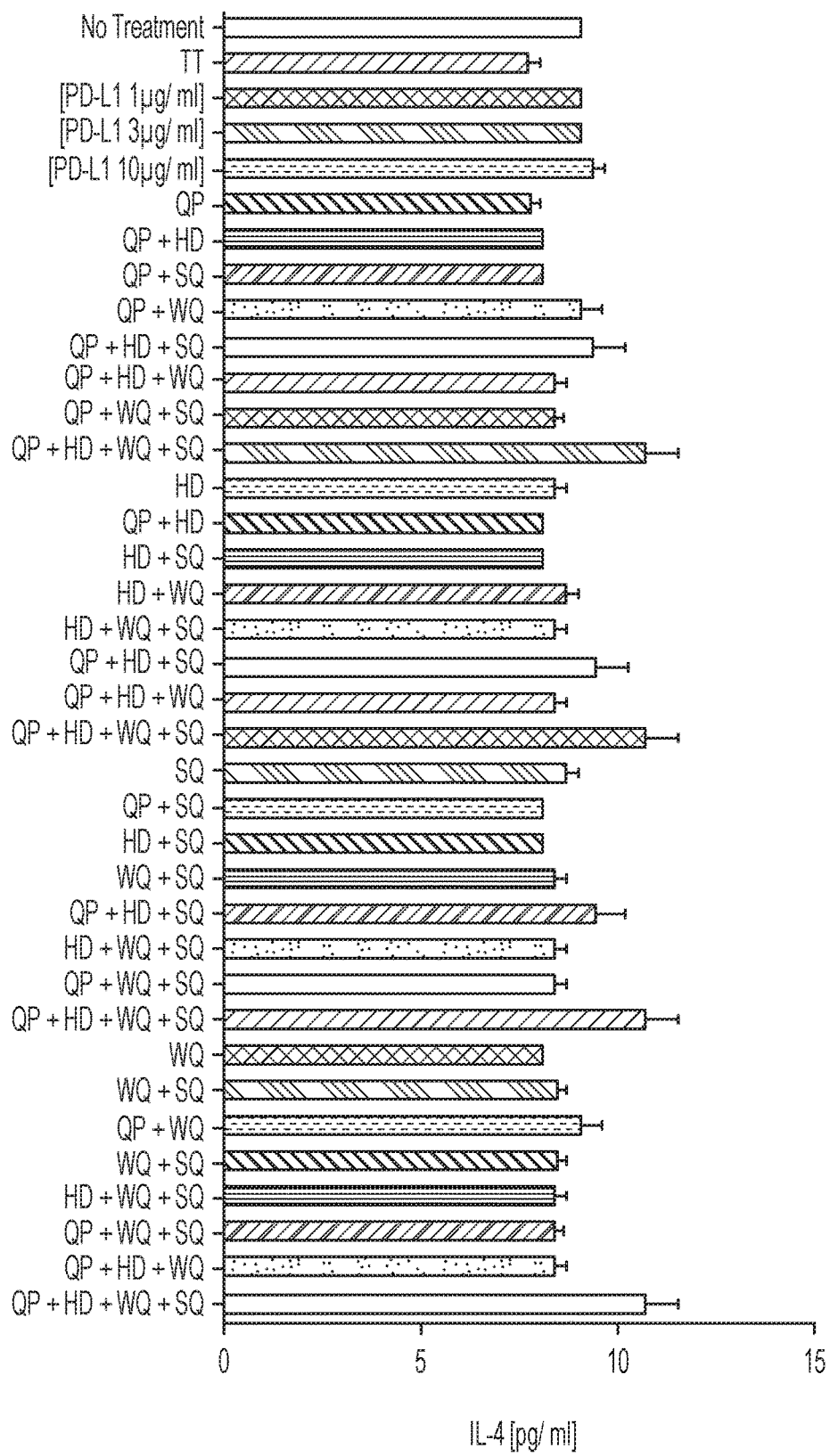
FIG. 17. Graph showing IL-4 production by PBMCs in a tetanus toxoid recall assay, after culture with various combinations of peptides QP20, HD20, WQ20, and SQ20.
Figure 18:
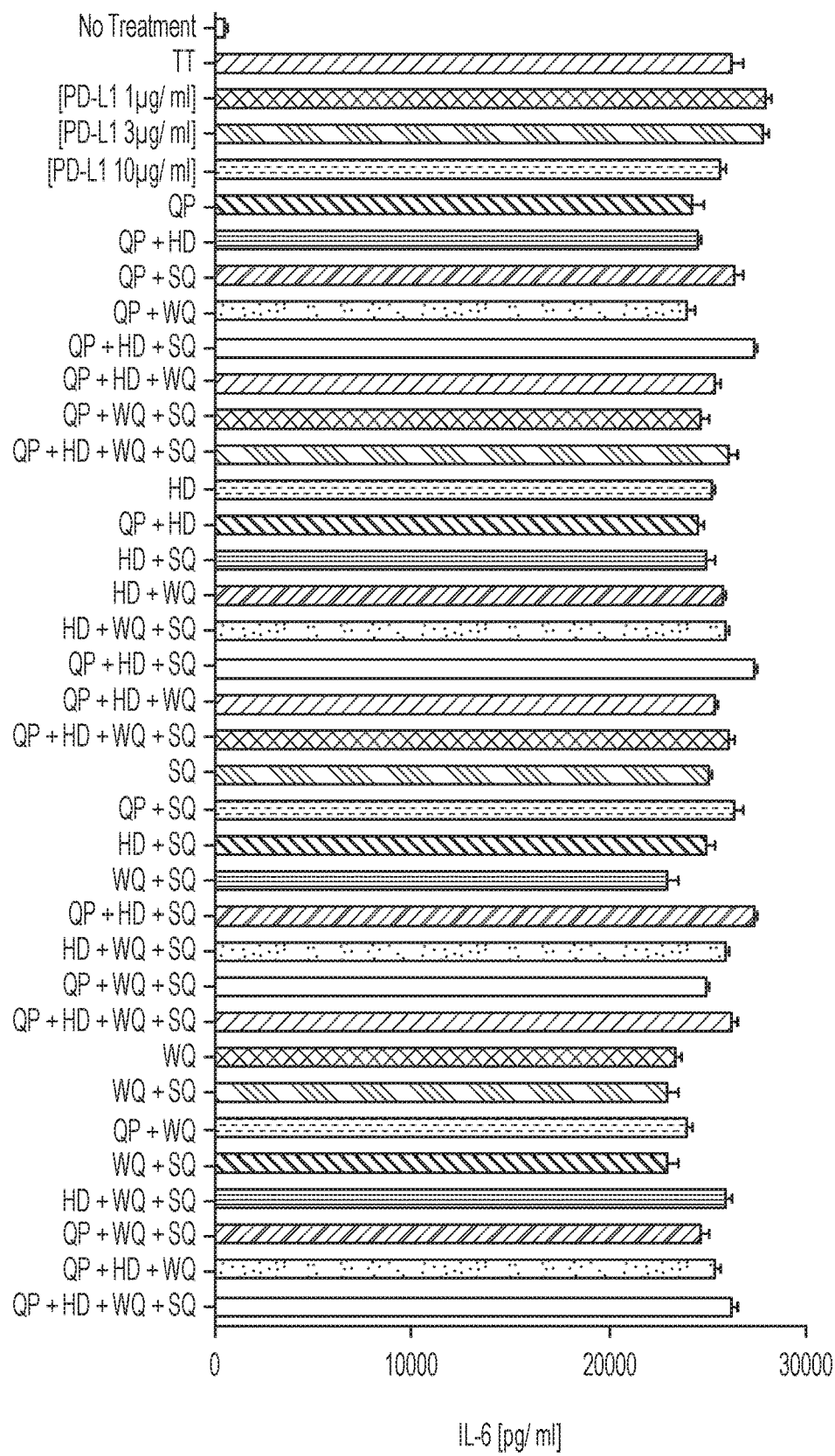
FIG. 18. Graph showing IL-6 production by PBMCs in a tetanus toxoid recall assay, after culture with various combinations of peptides QP20, HD20, WQ20, and SQ20.
Figure 19:
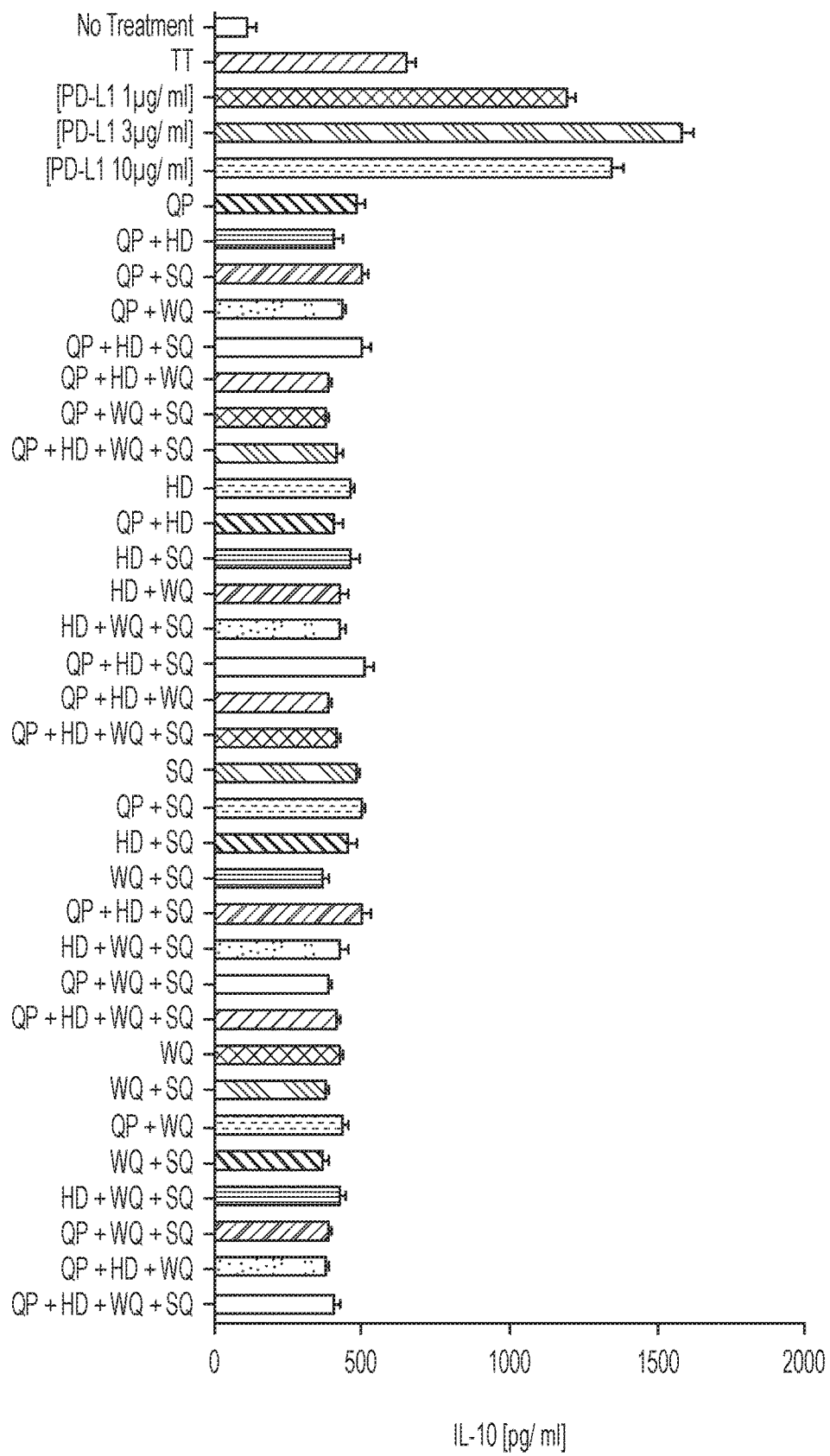
FIG. 19. Graph showing IL-10 production by PBMCs in a tetanus toxoid recall assay, after stimulation with various combinations of peptides QP20, HD20, WQ20, and SQ20.
Figure 20:
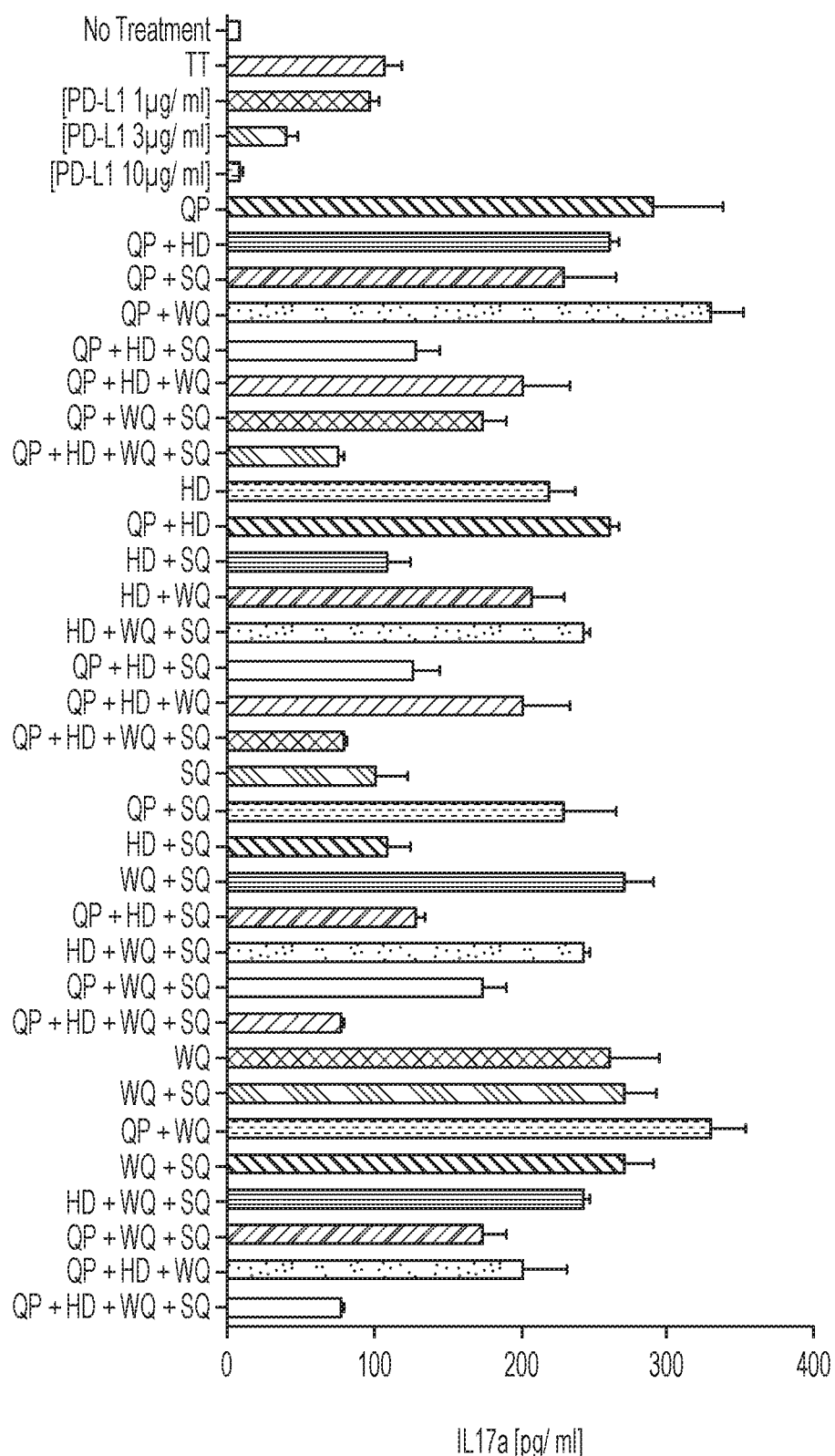
FIG. 20. Graph showing IL-17a production by PBMCs after stimulation with various combinations of peptides QP20, HD20, WQ20, and SQ20.
Figure 21:
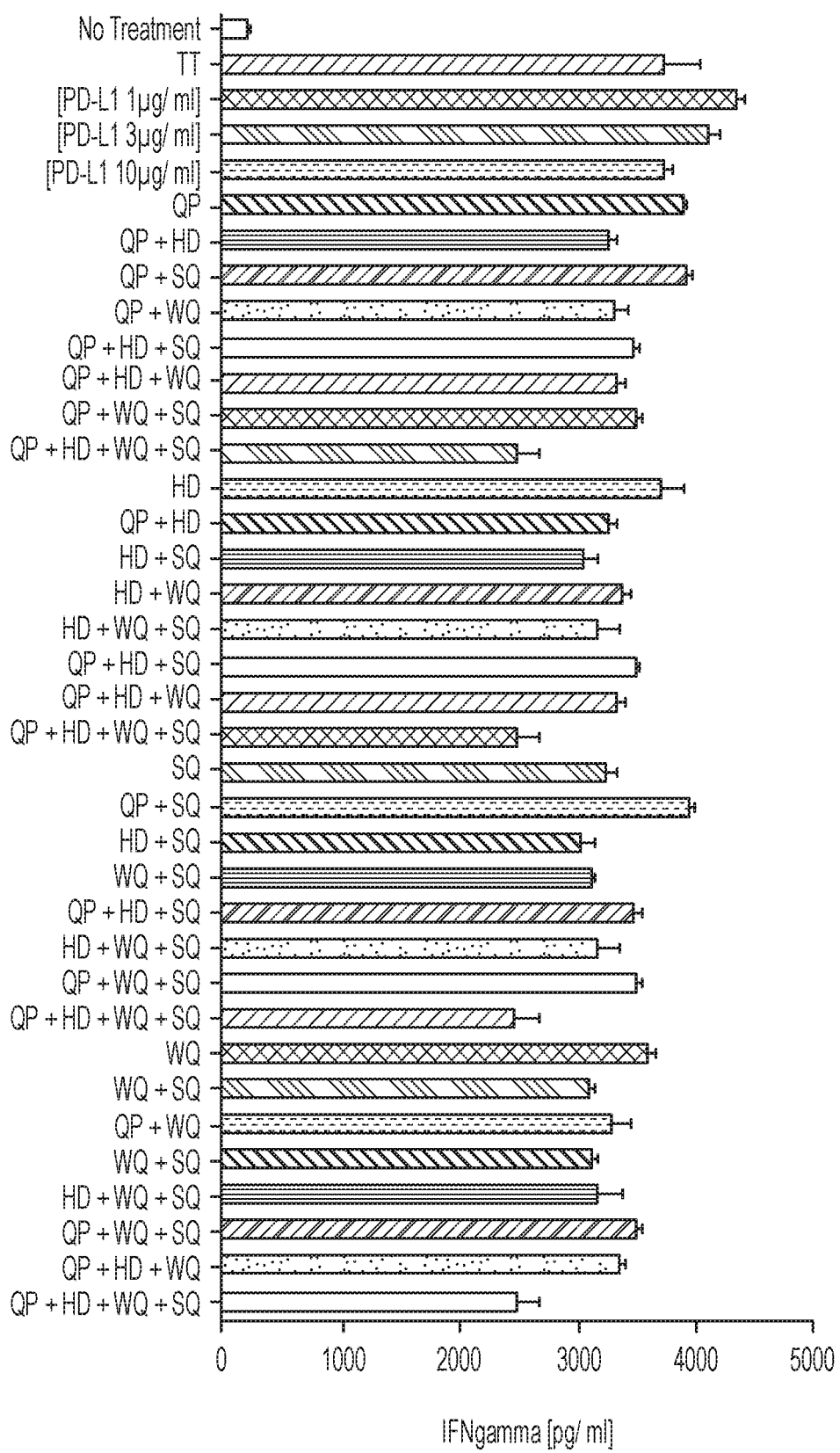
FIG. 21. Graph showing IFNγ production by PBMCs after culture with various combinations of peptides QP20, HD20, WQ20, and SQ20.
Figure 22:
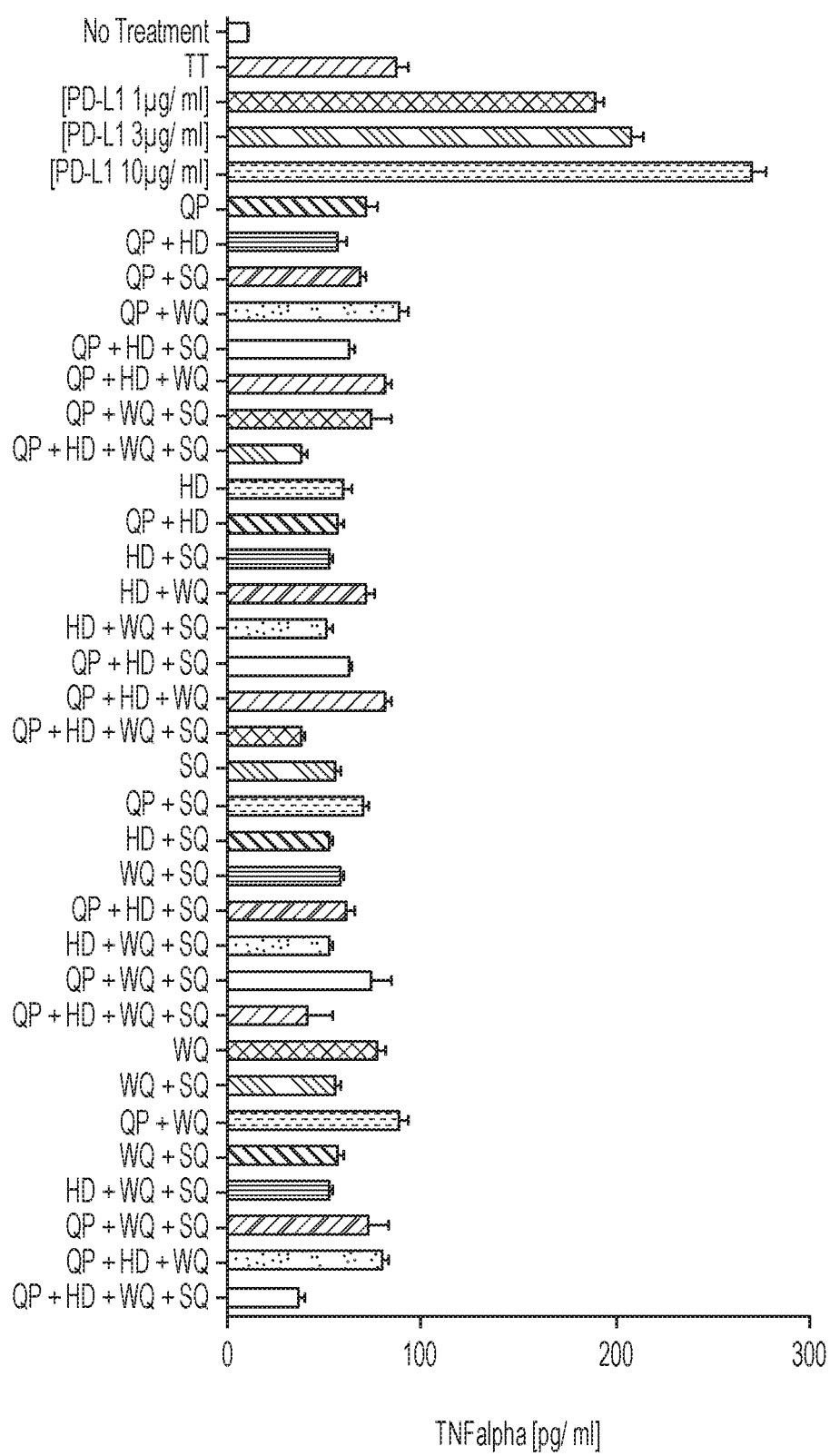
FIG. 22. Graph showing TNFα production by PBMCs after culture with various combinations of peptides QP20, HD20, WQ20, and SQ20.
Figure 23A:
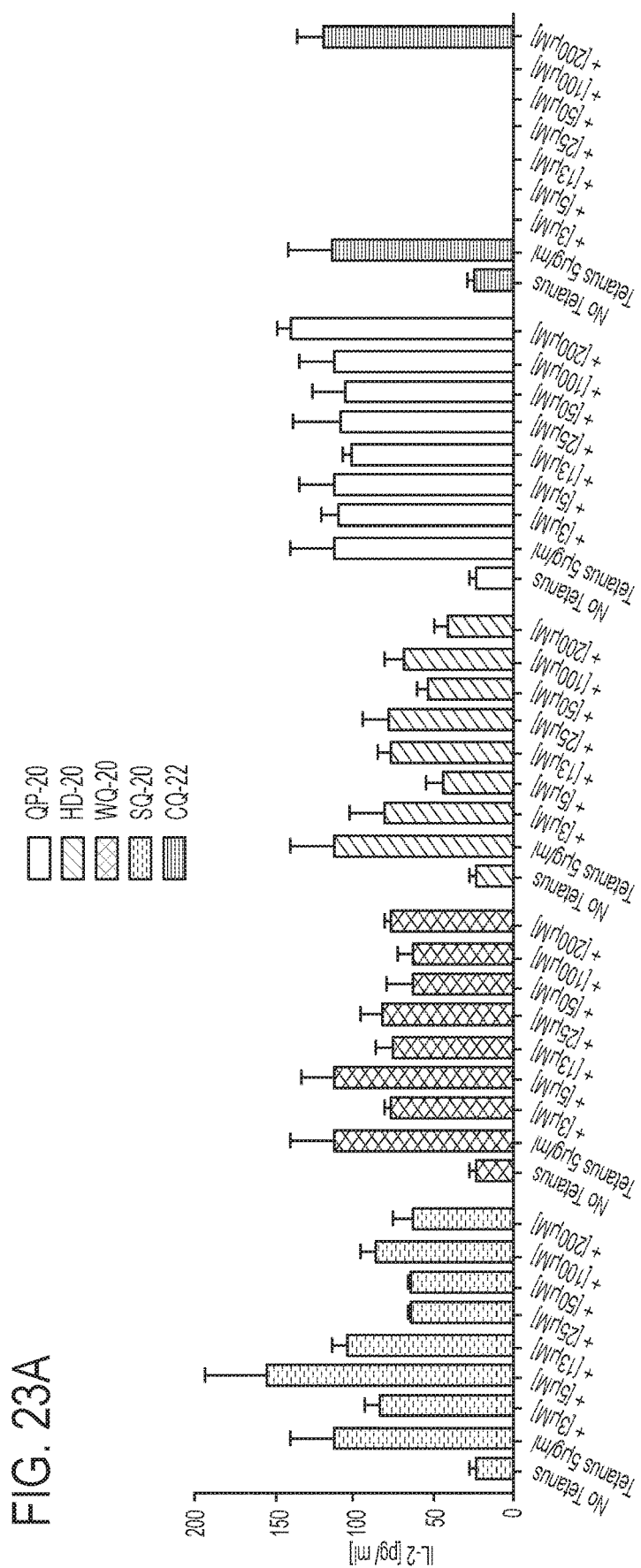
FIG. 23A. Graph showing IL-2 production by PBMCs from donor A after culture with peptides QP20, HD20, WQ20, and SQ20, or CQ-22.
Figure 23B:
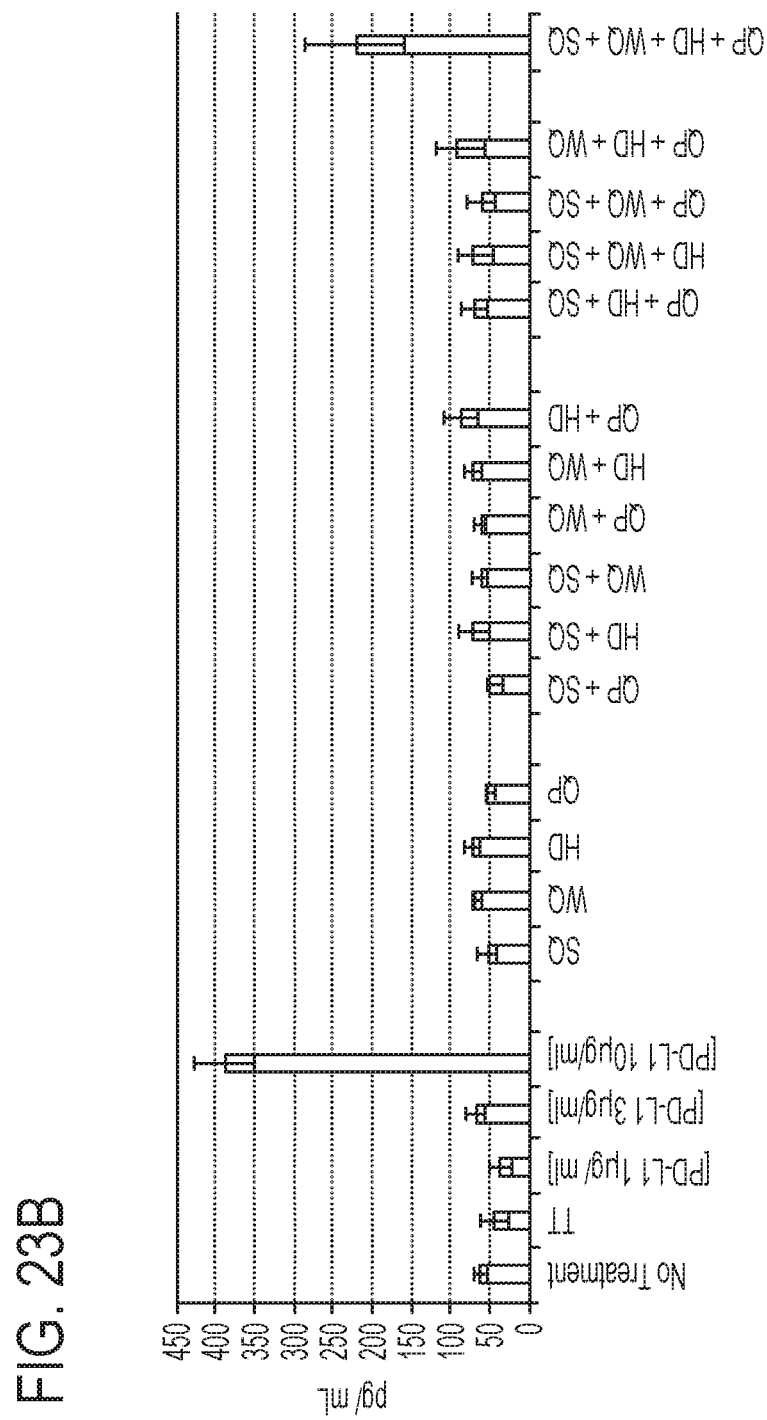
FIG. 23B. Graph showing IL-2 production by PBMCs from donor B after culture with peptides QP20, HD20, WQ20, or SQ20 and combinations of these peptides.
Figure 24A:
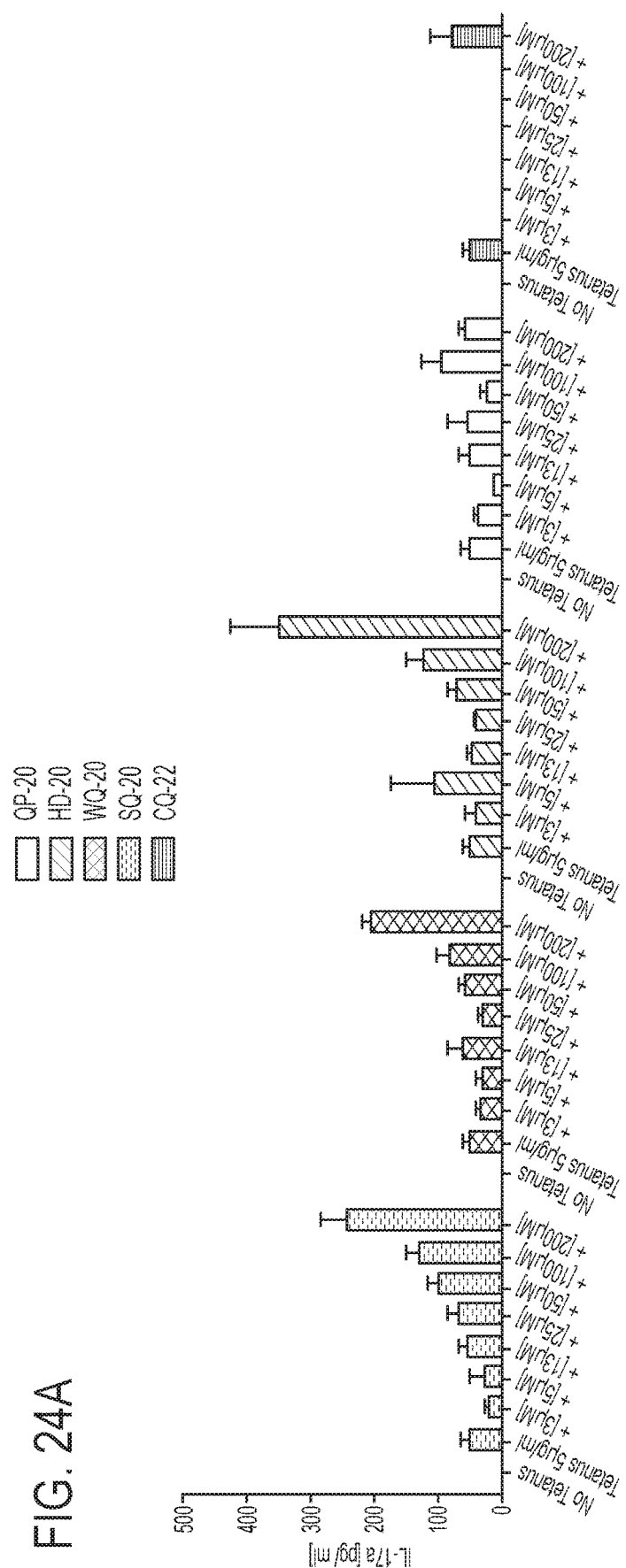
FIG. 24A. Graph showing IL-17a production by PBMCs from donor A after culture with peptides QP20, HD20, WQ20, and SQ20, or CQ-22.
Figure 24B:
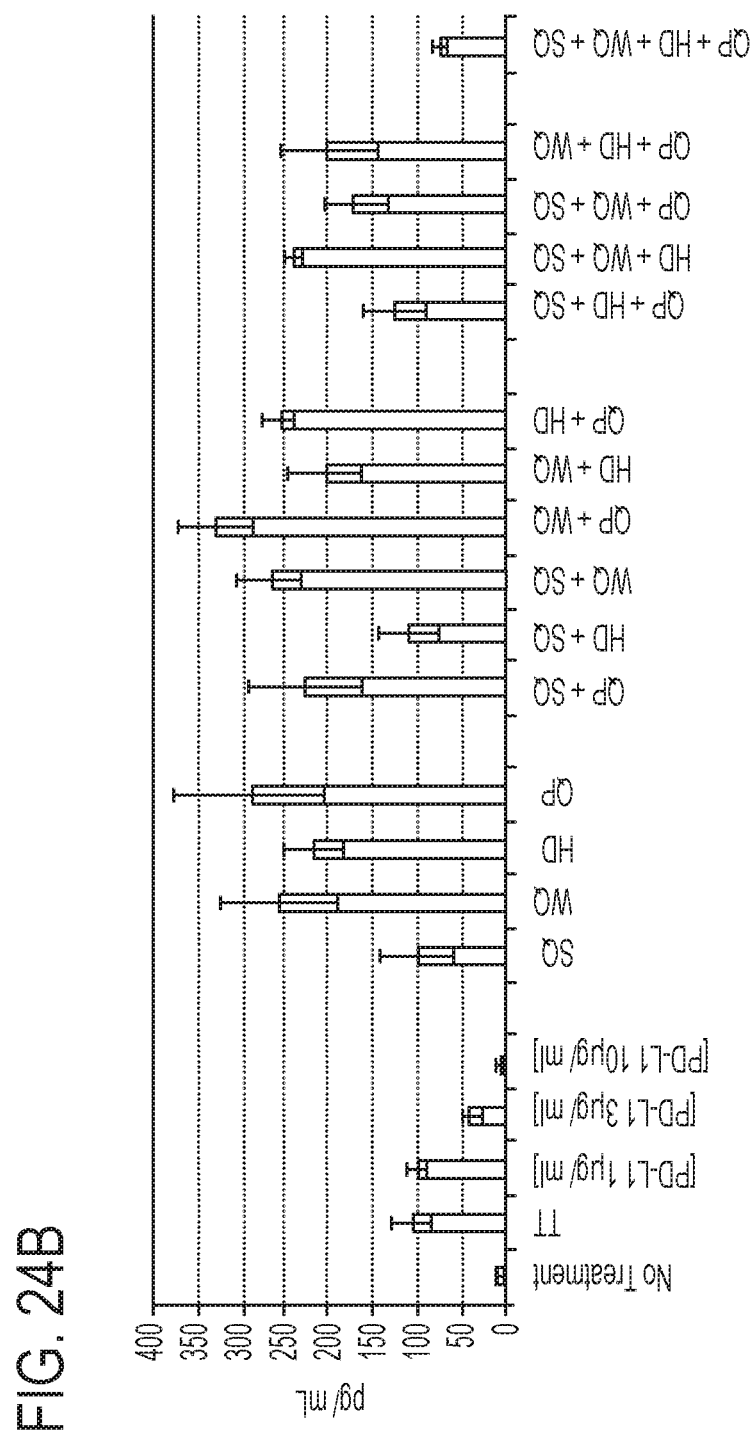
FIG. 24B. Graph showing IL-17a production by PBMCs from donor B after culture with peptides QP20, HD20, WQ20, or SQ20 and combinations of these peptides.

The results of assays of the peptides identified above are shown in FIGS. 8A-B. These results demonstrate that each of the four peptides restores luciferase expression in a dose-dependent manner, with peak-fold inhibition of approximately 1.5 at a concentration of approximately 25 µM.

Example 4. Tetanus Toxoid Recall Assay Using Individual Peptides

Peptides 1-4 were tested in a human PBMC-based tetanus antigen recall assay. "Peptide CQ-22" was used as a negative control.

PBMCs were obtained from plasma of human donors and tested in vitro for recall of tetanus toxoid. Suitable PBMCs were cryopreserved until needed, then thawed and cultured in a 96-wellplate. Tetanus toxoid was added to the cultures in the presence or absence of peptides 1-4, and the production of cytokines and cell surface T cell activation markers were examined.

The results of these assays are shown in FIGS. 9-15 and summarized qualitatively in Table 2. In the table, "x" indicates no effect, "−" indicates a possible low effect, "+" indicates some effect, and "++" indicates a definite effect.

TABLE 2

| peptide | IL-2 | IL-4 | IL-6 | IL-10 | IL-17a | IFNγ | TNFα |
|---|---|---|---|---|---|---|---|
| QP20 | x | − | x | x | x | x | x |
| HD20 | − | x | ++ | x | ++ | ++ | ++ |
| WQ20 | − | ++ | ++ | x | ++ | ++ | ++ |
| SQ20 | + | − | ++ | + | ++ | ++ | + |

The results demonstrated a trend towards modest enhancement of IL-6, IL-17α, IFNγ, and TNFα production at the highest concentrations of peptides. No significant enhancement of IL-2 production was detected.

Example 5. Tetanus Toxoid Recall Assay Using Combinations of Peptides

Combinations of peptides were tested in the antigen recall assay described above, using a different PBMC donor and a different lot number of tetanus toxoid. The results are shown in FIGS. 16, 17, 18, 19, 20, 21, and 22. These results demonstrated that the combination of the four peptides combination of the four peptides QP20, HD20, WQ20, and SQ20 result in increased IL-2 production and reduced IL-17a production.

The effect of peptides QP20, HD20, WQ20, and QP20 on the production of IL-2 and IL-17a appears to be donor-specific, as shown in FIGS. 23A-B and 24A-B.

Example 6. Biacore® Assays

BIACORE® assays were carried out using a BIACORE® T-200 at 25° C. The assay and regeneration buffers contained 10 mM HEPES (pH 7.4), 150 mM NaCl, 3 mM EDTA, and 0.05% P20. The immobilization buffer was 10 mM sodium acetate, pH 5.0. The flow rate used for immobilizing the ligand was 5 µl/min. The flow rate for kinetics analysis was 30 µl/min.

Scouting.

12,000 response units (RU) of human and 6000 RU of mouse PD-1 receptors were directly immobilized on flow cell 2 and flow cell 4 of the CMS chip by amine coupling method (EDC/NHS). The un-occupied sites were blocked with 1M ethanol amine. Scouting was performed at a single analyte concentration of 25 µM to confirm yes/no binding. Flow cell 1 was kept blank and used for reference subtraction. Binding of analyte to the ligand was monitored in real time.

Full Kinetics.

Based on the scouting results, full kinetics were performed by immobilizing higher RU of the ligand to a new chip and analyte concentration at 25 µM, followed by serial dilution to 12.5, 6.25, 3.125, 1.562, 0.78 and 0 µM concentration or as indicated. Due to fast on rate and off rate, KD was determined by steady state equilibrium kinetics.

Chi square ($\chi 2$) analysis was carried out between the actual sensorgram and a sensorgram generated from the BIANALYSIS® software (black line) to determine the accuracy of the analysis. A $\chi 2$ value within 1-2 is considered significant (accurate) and below 1 is highly significant (highly accurate). The results are summarized in Table 3.

TABLE 3

| Ligand 10,000 RU | Analyte | Rmax (RU) | KA (1/M) | KD (M) | Conc. (µM) | $\chi^2$ |
|---|---|---|---|---|---|---|
| mouse PD-1 | WQ-21 | 270 | $1.31 \times 10^3$ | $7.61 \times 10^{-4}$ | 0-25 | 0.0203 |
| mouse PD-1 | QP-20 | 13.4 | $1.80 \times 10^4$ | $5.54 \times 10^{-5}$ | 0-25 | 0.0446 |
| mouse PD-1 | HD-20 | 76 | $4.25 \times 10^3$ | $2.35 \times 10^{-4}$ | 0-25 | 0.11 |
| mouse PD-1 | SQ-20 | 12.8 | $2.14 \times 10^4$ | $4.68 \times 10^{-5}$ | 0-25 | 0.039 |
| human PD-1 | WQ-21 | 84.7 | $3.28 \times 10^3$ | $3.05 \times 10^{-4}$ | 0-25 | 0.0309 |
| human PD-1 | QP-20 | 3.83 | $9.36 \times 10^4$ | $1.07 \times 10^{-5}$ | 0-25 | 0.0569 |
| human PD-1 | HD-20 | 3.35 | $3.18 \times 10^5$ | $3.41 \times 10^{-6}$ | 0-12.5 | 0.0733 |
| human PD-1 | SQ-20 | 4.05 | $1.94 \times 10^5$ | $5.16 \times 10^{-6}$ | 0-25 | 0.111 |
| mouse PD-1 | Mouse PD-L1 | 259 | $2.75 \times 10^6$ | $3.64 \times 10^{-7}$ | 0-50 | 0.105 |
| human PD-1 | Human PD-L1 | 213 | $6.92 \times 10^6$ | $1.44 \times 10^{-7}$ | 0-50 | 2.44 |

These results indicate that each of the four peptides bind both human and mouse PD-1. QP20 and SQ20 showed the highest affinity towards mouse PD-1. HD20 and SQ20 showed the highest affinity towards human PD-1.

Example 7. Experimental Metastasis Model

Efficacy of the peptides was evaluated in a B16-F10-LacZ experimental metastasis model. In this model, B16-F10-LacZ cells, transfected to express the LacZ gene that encodes β-galactoside, an intracellular enzyme, are injected into the tail vein of syngeneic mice. The cells travel through the circulation, settle in the lungs, and form tumors. Mice are terminated 2 weeks after implant. When the enzyme cleaves its substrate, X-gal, the products dimerize and change color and can be detected ex vivo. The number of metastatic tumors on the surface of the lung is then quantified by manual counting of tumors under a dissecting microscope.

Briefly, mice (N=7) were implanted on study day 0 with B16-F10-LacZ tumor cells ($5 \times 10^5$ or $1 \times 10^6$ cells per mouse) by intravenous injection in the tail vein. Mice received a treatment of the peptide combination (200 μg, 20 μg, or 2 μg, each peptide per dose) intravenously by tail vein injection on study days 2, 5, 7, 9 and 12. Detailed clinical examinations and body weights were recorded regularly during treatment. Mice were terminated on study day 14, and their lungs were removed and stained. The number of tumor metastases were counted. Treatment groups are described in Table 4.

TABLE 4

| Group | N | Implant | Treatment | Dose | Route | Treatment Days |
|---|---|---|---|---|---|---|
| 1 | 7 | $5 \times 10^5$ | QP-20, SQ-20, HD-20, WQ-20 | 200 μg | IV | SD 2, 5, 7, 9, 12 |
| 2 | 7 | $5 \times 10^5$ | QP-20, SQ-20, HD-20, WQ-20 | 20 μg | IV | SD 2, 5, 7, 9, 12 |
| 3 | 7 | $5 \times 10^5$ | QP-20, SQ-20, HD-20, WQ-20 | 2 μg | IV | SD 2, 5, 7, 9, 12 |
| 4 | 7 | $5 \times 10^5$ | Untreated | — | — | — |
| 5 | 7 | $1 \times 10^6$ | QP-20, SQ-20, HD-20, WQ-20 | 200 μg | IV | SD 2, 5, 7, 9, 12 |
| 6 | 7 | $1 \times 10^6$ | Untreated | — | — | — |

Figure 25:
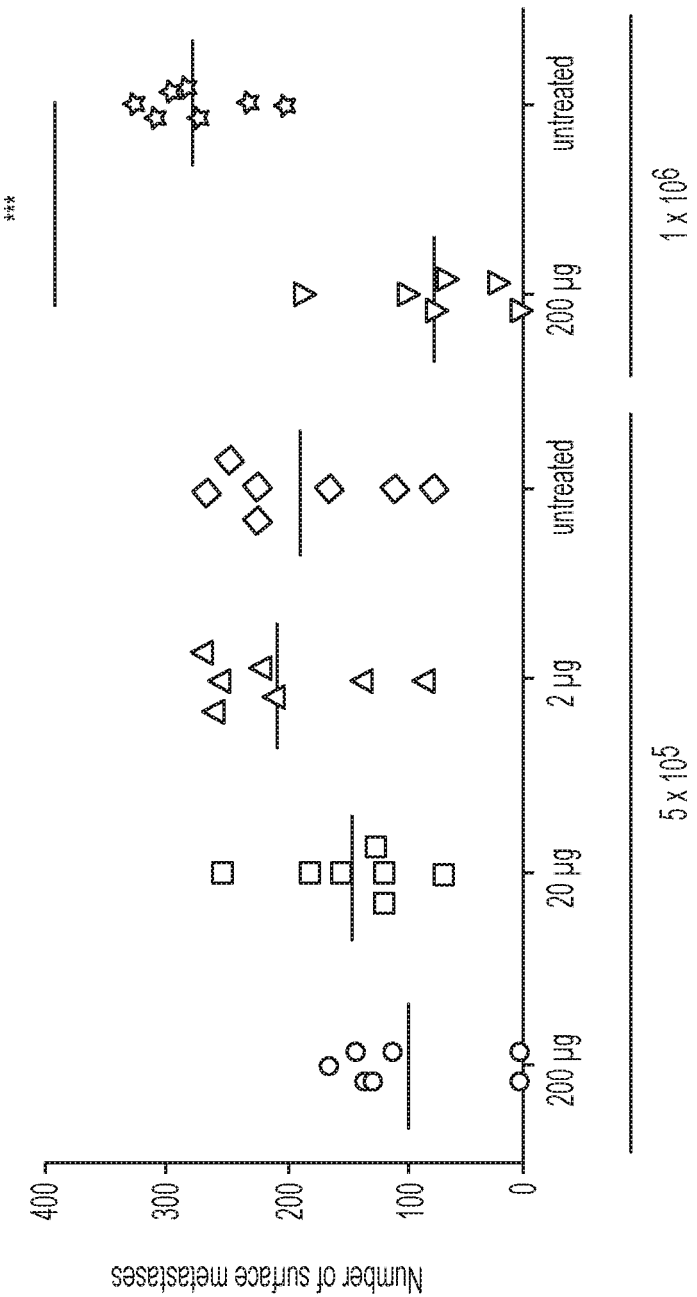
FIG. 25. Graph showing number of surface metastases in mice bearing B16-F10-LacZ tumor cells and treated with combinations of peptides.

The results are shown in FIG. 25. A good dose response was observed when mice were implanted at both cell concentrations. Mice treated with the highest dose of peptide mixture (200 μg) had the fewest tumors (average 97), and mice treated with the lowest dose of peptide mixture (2 μg) had the most tumors (average 205). Similarly, in the two groups that were implanted with high tumor numbers, the untreated group had significantly more tumors. This indicates that the 4 peptides in combination showed a dose-dependent efficacy on B16-F10-LacZ tumor growth in vivo. Moreover, the peptide combination was well tolerated by the mice and did not have any acute adverse effects on animal health.

Example 8. Effect of Peptide Combination on the Immunogenicity of a Malaria Vaccine Immunogenicity of the peptide combination as a prophylactic vaccine adjuvant was assessed in a mouse model of malaria. Balb/c mice immunized with an adenovirus-based malaria vaccine expressing the *Plasmodium yoelii* circumsporozoite protein (AdPyCS) were given 200 μg of the peptide combination, anti-PD-1 mAb, anti-PDL1 mAb, or the negative control peptide ovalbumin (OVA) on days 1, 3, 5, and 7 after immunization with AdPyCS (Table 5). Note that no additional adjuvant was added to the AdPyCS antigen. Spleens were collected 12 days after immunization, and the number of splenic PyCS-specific, IFNγ-secreting CD8+ T cells was determined via ELISpot assay. Note that for the ELISpot assay, splenocytes were stimulated with the SYVPSAEQI peptide (SEQ ID NO:5), an H-2Kd-restricted CD8+ T cell epitope of PyCS.

TABLE 5

| Cohort | Test Sample | # Mice | Route | Treatment days |
|---|---|---|---|---|
| 1 | AdPyCS only | 5 | — | — |
| 2 | AdPyCS + control OVA peptide (200 μg) | 5 | i.p. | 0, 1, 3, 5, 7 |
| 3 | AdPyCS + peptide combo (200 μg) | 5 | i.p. | 0, 1, 3, 5, 7 |
| 4 | AdPyCS + anti-PD-1 antibody (200 μg) | 5 | i.p. | 0, 1, 3, 5, 7 |
| 5 | AdPyCS + anti-PDL1 antibody (200 μg) | 5 | i.p. | 0, 1, 3, 5, 7 |

Figure 26:
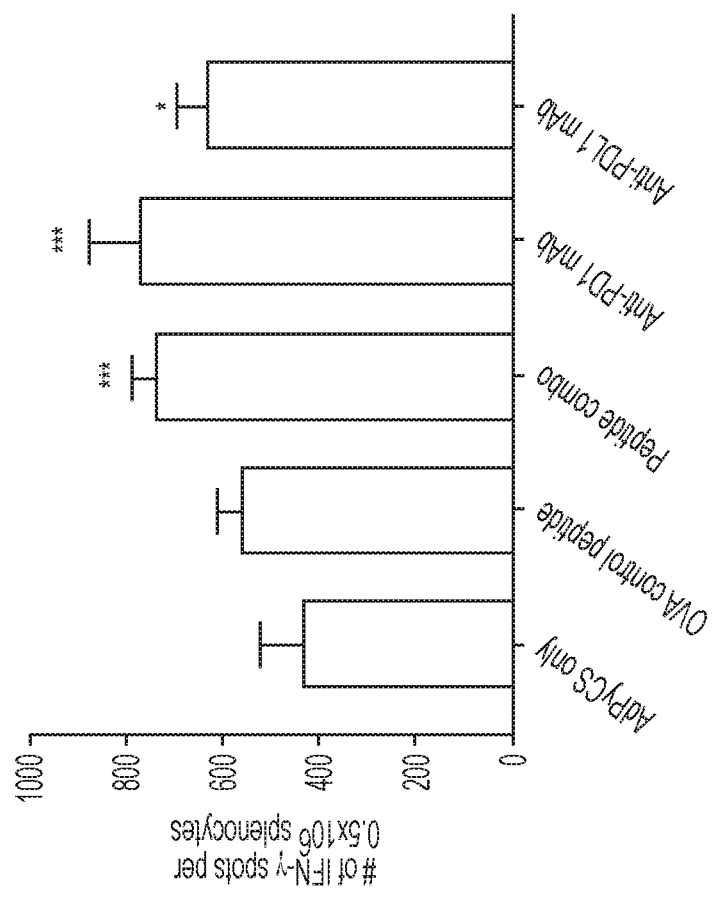
FIG. 26. Graph showing the average number±standard deviation of *Plasmodium yoelii* circumsporozoite protein (PyCS)-specific, IFNγ-secreting CD8 T cells per $0.5 \times 10^6$ splenocytes for each cohort tested in Example 8.

FIG. 26 shows the average number±standard deviation of CSP-specific, IFNγ-secreting CD8+ T cells per $0.5 \times 10^6$ splenocytes for each cohort. Significant differences in the average number±standard deviation of CSP-specific, IFNγ-secreting CD8+ T cells per $0.5 \times 10^6$ splenocytes between the AdPyCS alone (Cohort 1) and the peptide combination (Cohort 3), anti-PD-1 antibody (Cohort 4) or anti-PD-L1 antibody (Cohort 5) were detected using the one-way ANOVA test (***$p<0.001$, and *$p<0.05$). These results demonstrate that the peptide combination (Cohort 3) is functionally active in vivo, increasing the number of CSP-specific, IFNγ-secreting CD8+ T cells ~1.6-fold relative to AdPyCS alone (Cohort 1), which was similar to changes with anti-PD-1 or -PD-L1 antibody (Cohort 4 and 5).

Example 9. Effect of Peptide Combination on Survival in a Model of Sepsis

Sepsis can negatively alter T cell function and survival, however this can be reversed when the PD-1:PDL1 interaction is blocked, which results in improved survival. Thus the efficacy of the peptide combination was assessed in a representative, clinically relevant model of sepsis where CD1 mice are subjected to cecal ligation and puncture (CLP) to induce intra-abdominal peritonitis. For this study, 200 μg of either the peptide combination or anti-PD-1 antibody were administered i.v. at 2, 24, 48, 72 and 96 hours after surgery. A vehicle control group was also included. Six mice were in each group. All mice were checked twice daily for signs of morbidity and mortality. Administration of the peptide combination conferred an enhanced survival advantage over the vehicle control group where the peptide combination showed a 2-fold higher survival rate (Table 6). Moreover, survival in the peptide combination group was slightly above treatment with anti-PD-1 antibody.

TABLE 6

| Group | % Survival |
|---|---|
| Vehicle Control | 50% |
| Anti-PD-1 antibody | 83% |
| PD-1 Peptide Combo | 100% |

Example 10. Effect of Peptide Combination on Serum HBsAg Levels in HBV-Infected Mice The combination of QP20, HD20, WQ20, and SQ20 peptides was assessed in a hepatitis B virus (HBV) mouse model where the role of PD-1 in T cell exhaustion and immunotolerance is documented (Tzeng et al., 2012; Ye et al., 2015). PD-1 is elevated in the hepatic T cells of mice with persistent HBV infection but not in animals that have cleared the infection. In this model, it has been shown that inhibition of the PD-1/PD-L1 interaction with an anti-PD-1 mAb both increases antigen-specific IFNγ production by hepatic T cells and reverses HBV persistence (Tzeng et al., 2012). This mouse model of persistent HBV presented an opportunity to test whether the combination of QP20, HD20, WQ20, and SQ20 peptides can reverse T cell exhaustion in vivo and aid the immune system in controlling viral infection.

Figure 27:
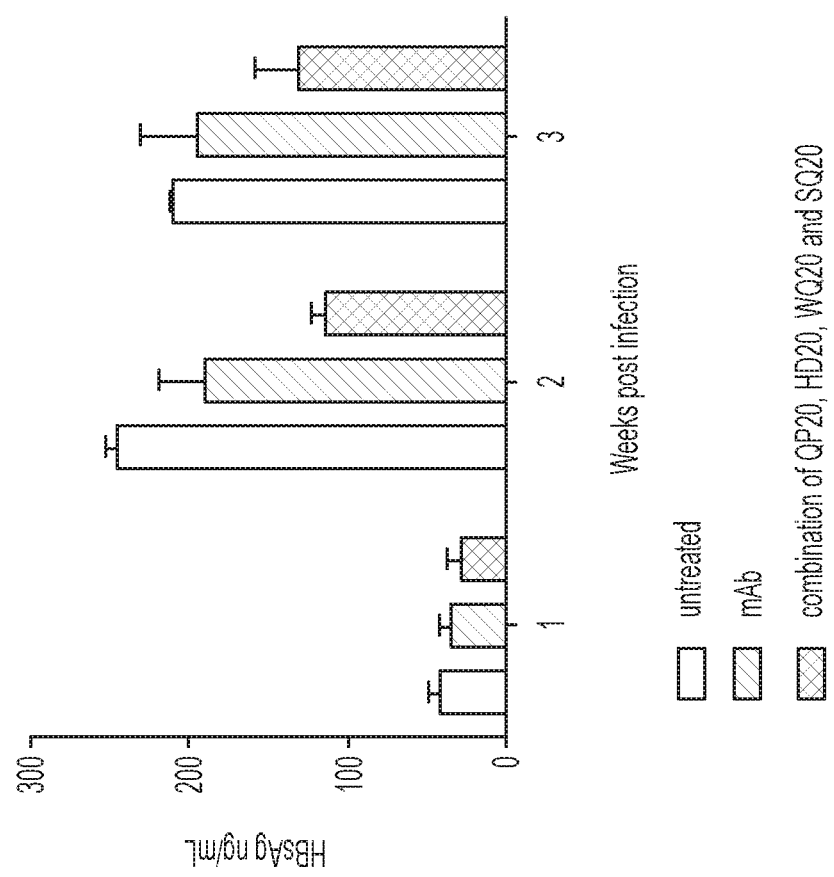
FIG. 27. Graph showing the effect of the combination of QP20, HD20, WQ20, and SQ20 peptides on the mean level of serum HBsAg (hepatitis B surface antigen) at weeks 2 and 3 post infection.

Mice infected with HBV were treated with saline (negative control), 200 µg of QP20, HD20, WQ20, and SQ20 peptides combined, or 200 µg anti-PD-1 mAb at 9 time points, 2 days prior to infection and days 1, 3, 6, 9, 12, 14, 17 and 20 post infection. The level of serum HB surface antigen (HBsAg) was monitored by ELISA on days 7, 14, and 21 to follow the infection (higher levels of serum HBsAg are reflective of higher viral titer) and detect the immune enhancement activity of the combination of QP20, HD20, WQ20, and SQ20 peptides. The group treated with the combination of QP20, HD20, WQ20, and SQ20 peptides showed significantly lower mean level of serum HBsAg at weeks 2 and 3 post infection (p<0.05, 1-way ANOVA, Tukey's Multiple Comparison Test) compared to the saline negative control (FIG. 27).

REFERENCES

Adams et al., "Big opportunities for small molecules in immuno-oncology," Nature Reviews Drug Discovery Advance Online Publication, Jul. 31, 2016, 20 pages Alsaab et al., "PD-1 and PD-L1 Checkpoint Signaling Inhibition for Cancer Immunotherapy: Mechanism, Combinations, and Clinical Outcome," Front. Pharmacol. 8, 561, 2017

Beavis et al., "Adenosine Receptor 2A Blockade Increases the Efficacy of Anti-PD-1 through Enhanced Anti-tumor T-cell Responses," Cancer Immunol. Res. 3, 506-17, 2015

Behlke, "Chemical modification of siRNAs for in vivo use," Oligonucleotides. 2008; 18:305-19.

Bensinger et al., "A phase 1 study of lucatumumab, a fully human anti-CD40 antagonist monoclonal antibody administered intravenously to patients with relapsed or refractory multiple myeloma," Br J Haematol. 159, 58-66, 2012.

Benson & Caligiuri, "Killer Immunoglobulin-like Receptors and Tumor Immunity," Cancer Immunol Res 2014; 2:99-104

Bodanszky et al., Peptide Synthesis, John Wiley and Sons, 2d ed. (1976)

Bramsen et al., "A large-scale chemical modification screen identifies design rules to generate siRNAs with high activity, high stability and low toxicity," Nucleic Acids Res. 2009; 37:2867-81.

Bruno et al., "Basics and recent advances in peptide and protein drug delivery," Ther. Deliv. 4, 1443-67, 2013

Bu et al., "Learning from PD-1 Resistance: New Combination Strategies," Trends Mol. Med. 22, 448-51, 2016

Burnett & Rossi, "RNA-based Therapeutics—Current Progress and Future Prospects," Chem Biol. 19, 60-71, 2012

Cao, "Advances in Delivering Protein and Peptide Therapeutics," Pharmaceutical Technology 40, 22-24, Nov. 2, 2016

Cherkassky et al., "Human CAR T cells with cell-intrinsic PD-1 checkpoint blockade resist tumor-mediated inhibition," J. Clin. Invest. 126, 3130-44, 2016

Chiu et al., "siRNA function in RNAi: a chemical modification analysis," RNA 2003; 9:1034-48.

Chong et al., "PD-1 blockade modulates chimeric antigen receptor (CAR)-modified T cells: refueling the CAR," Blood. 129(8), 1039-41, 2017, published on-line Dec. 28, 2016

Chowdhury et al., "Combination therapy strategies for improving PD-1 blockade efficacy: a new era in cancer immunotherapy," J. Int. Med. doi: 10.1111/joim.12708, Epub ahead of print, Oct. 26, 2017

Creative Biolabs User Manual, "TriCo-20™ Phage Display 20-mer Random Peptide Library," 14 pages, Aug. 4, 2009

Dempke et al., "Second- and third-generation drugs for immuno-oncology treatment—The more the better?" Eur. J. Cancer 74, 55-72, March 2017

Differding, "AUNP-12—A Novel Peptide Therapeutic Targeting PD-1 Immune Checkpoint Pathway for Cancer Immunotherapy—Structure Activity Relationships & Peptide/Peptidomimetic Analogs," available at differding.com/data/AUNP_12_A_novel_peptide_therapeutic_targeting_PD_1_immune_checkpoint_pathway_for_cancer_immunotherapy.pdf, Feb. 26, 2014

Duraiswamy et al., "Dual Blockade of PD-1 and CTLA-4 Combined with Tumor Vaccine Effectively Restores T-Cell Rejection Function in Tumors," Cancer Res 73, 3591-603, 2013

Feridooni et al., "Noninvasive Strategies for Systemic Delivery of Therapeutic Proteins—Prospects and Challenges," Chapter 8 of Sezer, ed., Smart Drug Delivery System, available at http://www.intechopen.com/books/smart-drug-delivery-system, Feb. 10, 2016

Gao et al., "VISTA is an inhibitory immune checkpoint that is increased after ipilimumab therapy in patients with prostate cancer," Nature Med. 23, 551-55, 2017

Harvey et al., "Efficacy of anti-ICOS agonist monoclonal antibodies in preclinical tumor models provides a rationale for clinical development as cancer immunotherapeutics," Journal for ImmunoTherapy of Cancer 3(Suppl 2), O9, 2015

He et al., "Lymphocyte-activation gene-3, an important immune checkpoint in cancer," Cancer Sci. 107, 1193-97, 2016

Huseni et al., "Anti-tumor efficacy and biomarker evaluation of agonistic anti-OX40 antibodies in preclinical models," Journal for ImmunoTherapy of Cancer 2(Suppl 3), P105, 2014

Infante et al., "A phase Ib dose escalation study of the OX40 agonist MOXR0916 and the PD-L1 inhibitor atezolizumab in patients with advanced solid tumors," J Clin Oncol. 34 (suppl; abstr 101), 2016

John et al., "Blockade of PD-1 immunosuppression boosts CAR T-cell therapy," OncoImmunology 2, e26286, 3 pages, 2013

Johnson et al., "Clinical and Biological Effects of an Agonist Anti-CD40 Antibody: A Cancer Research UK Phase I Study," Clin Cancer Res 21, 1321-28, 2015

Johnson et al., "A Cancer Research UK phase I study evaluating safety, tolerability, and biological effects of chimeric anti-CD40 monoclonal antibody (MAb), Chi Lob 7/4," J Clin Oncol. 28, 2507, 2010.

Judge & MacLachlan, "Overcoming the innate immune response to small interfering RNA," Hum Gene Ther. 2008; 19:111-24.

Kaczmarek et al., "Advances in the delivery of RNA therapeutics: from concept to clinical reality," Genome Medicine 2017; 9:60, 16 pages Kauffman et al., "Efficacy and immunogenicity of unmodified and pseudouridine-modified mRNA delivered systemically with lipid nanoparticles in vivo," Biomaterials. 2016; 109:78-87.

Kavikansky & Pavlick, "Beyond Checkpoint Inhibitors: The Next Generation of Immunotherapy in Oncology," Amer. J. Hematol. Oncol. 13, 9-20, 2017

Khubchandani et al., "Dacetuzumab, a humanized mAb against CD40 for the treatment of hematological malignancies," Curr Opin Investig Drugs 10, 579-87, 2009.

Kontermann, "Half-life extended biotherapeutics," Expert Opin. Biol. Ther. 16, 903-15, 2016.

Le Mercier et al., "VISTA Regulates the Development of Protective Antitumor Immunity," Cancer Res 2014; 74:1933-1944

Leone et al., "A2aR antagonists: Next generation checkpoint blockade for cancer immunotherapy," Computational and Structural Biotechnology Journal 13, 265-72, 2015

Li et al., "Discovery of peptide inhibitors targeting human programmed death 1 (PD-1) receptor," Oncotarget 7, 64967-76, Aug. 12, 2016

Li et al., "Effects of chemically modified messenger RNA on protein expression," Bioconjug Chem. 2016; 27:849-53.

Linch et al., "OX40 agonists and combination immunotherapy: putting the pedal to the metal," Frontiers in Oncology 5, 14 pages, 2015

Liu et al., "Immune-checkpoint proteins VISTA and PD-1 nonredundantly regulate murine T-cell responses," Proc. Nat'l. Acad. Sci. USA 112, 6682-87, 2015

Magiera-Mularz et al., "Bioactive macrocyclic inhibitors of the PD-1/PD-L1 immune checkpoint," Angewandte Chemie Int. Ed. 10.1002/anie.201707707, e-published Sep. 26, 2017

Maute et al., "Engineering high-affinity PD-1 variants for optimized immunotherapy and immuno-PET imaging," Proc. Natl. Acad. Sci. USA, E6506-E6514, published online Nov. 10, 2015

McOmie, Protective Groups in Organic Chemistry, Plenum Press, New York, N.Y., 1973

Mediavilla-Varela et al., "A Novel Antagonist of the Immune Checkpoint Protein Adenosine A2a Receptor Restores Tumor-Infiltrating Lymphocyte Activity in the Context of the Tumor Microenvironment," Neoplasia 19, 530-36, 2017

Mellemgaard et al., "Combination immunotherapy with IDO vaccine and PD-1 inhibitors in advances HSCLC," DOI: 10.1200/JCO.2017.35.15_suppl.TPS2610 Journal of Clinical Oncology 35, no. 15_suppl—published online before print, 2017

Merrifield, J. Am. Chem. Soc. 85:2149-54, 1963

Messenheimer et al., "Timing of PD-1 Blockade Is Critical to Effective Combination Immunotherapy with Anti-OX40," Clin. Cancer Res. 23, DOI: 10.1158/1078-0432.CCR-16-2677 Published October 2017

Michaelson et al., "Preclinical evaluation of JTX-2011, an anti-ICOS agonist antibody,", Abstract 573, Proceedings: AACR 107th Annual Meeting 2016; Apr. 16-20, 2016; New Orleans, La.

Morrissey et al., "Immunotherapy and Novel Combinations in Oncology: Current Landscape, Challenges, and Opportunities," Clinical and Translational Science 9, 89-104, 2016

Morrissey et al., "Potent and persistent in vivo anti-HBV activity of chemically modified siRNAs," Nat Biotechnol. 2005; 23:1002-7.

Neurath et al., eds., The Proteins, Vol. II, 3d ed., pp. 105-237, Academic Press, New York, N.Y. (1976)

Ott et al., "Combination immunotherapy: a road map," J. ImmunoTherapy of Cancer 5, 16, 2017

Patel et al., "Recent Advances in Protein and Peptide Drug Delivery: A Special Emphasis on Polymeric Nanoparticles," Protein. Pept. Lett. 21, 1102-20, 2014

Penchala et al., "A biomimetic approach for enhancing the in vivo half-life of peptides," Nat. Chem. Biol. 11, 793-98, 2015.

Prakash et al., "Positional effect of chemical modifications on short interference RNA activity in mammalian cells," J Med Chem. 2005; 48:4247-53.

Pratt & MacRae, "The RNA-induced silencing complex: a versatile gene-silencing machine," J Biol Chem. 2009; 284:17897-901.

Rivera et al., "Hair Repigmentation During Immunotherapy Treatment With an Anti-Programmed Cell Death 1 and Anti-Programmed Cell Death Ligand 1 Agent for Lung Cancer," JAMA Dermatol. 2017 Jul. 12. doi: 10.1001/jamadermatol.2017.2106, Jul. 12, 2017

Sahin et al., "mRNA-based therapeutics—developing a new class of drugs," Nat Rev Drug Discov. 2014; 13:759-80.

Sakuishi et al., "Targeting Tim-3 and PD-1 pathways to reverse T cell exhaustion and restore anti-tumor immunity," J. Exp. Med. 20, 2187-94, 2010

Schaer et al., "Modulation of GITR for cancer immunotherapy," Curr Opin Immunol. 24, 217-24, 2012

Sharma & Allison, "Immune Checkpoint Targeting in Cancer Therapy: Toward Combination Strategies with Curative Potential," Cell 161, 205-14, 2015

Shindo et al., "Combination Immunotherapy with 4-1BB Activation and PD-1 Blockade Enhances Antitumor Efficacy in a Mouse Model of Subcutaneous Tumor," Anticancer Res. 35, 129-36, 2015

Shrimali et al., "Concurrent PD-1 Blockade Negates the Effects of OX40 Agonist Antibody in Combination Immunotherapy through Inducing T-cell Apoptosis," Cancer Immunol Res 5(9), pages OF1-12, Aug. 28, 2017

Skalniak et al., "Small-molecule inhibitors of PD-1/PD-L1 immune checkpoint alleviate the PD-L1-induced exhaustion of T-cells," Oncotarget, Advance Publications, Aug. 7, 2017, 15 pages Smith, "Pigmented skin lesions lightened during melanoma immunotherapy," http://www.mdedge.com/edermatologynews/article/132598/melanoma/pigmented-skin-lesions-lightened-during-melanoma, Mar. 2, 2017

Soutschek et al., "Therapeutic silencing of an endogenous gene by systemic administration of modified siRNAs," Nature. 2004; 432:173-78.

Spodzieja et al., "Design of short peptides to block BTLA/HVEM interactions for promoting anticancer T-cell responses," PLoS ONE 12(6): e0179201, 17 pages, 2017

Stuart & Young, Solid Phase Peptide Synthesis, Pierce Chemical Company, Rockford, Ill., 1984

Tigue et al., "MEDI1873, a potent, stabilized hexameric agonist of human GITR with regulatory T-cell targeting potential," ONCOIMMUNOLOGY 6(3), e1280645 (14 pages), Feb. 3, 2017

Triebel et al., "LAG-3, a novel lymphocyte activation gene closely related to CD4," J. Exp. Med. 171, 1393-405, 1990

Tuck, "Development of Small Molecule Checkpoint Inhibitors," Immune Checkpoint Inhibitors Symposium, 28 pages, Mar. 14-16, 2017

Tzeng et al., "PD-1 blockage reverses immune dysfunction and hepatitis B viral persistence in a mouse animal model," PLoS One 7(6):e39179, 2012.

Van Dessel et al., "Potent and tumor specific: arming bacteria with therapeutic proteins," Ther. Deliv. 6, 385-99, 2015.

Vonderheide and Glennie, "Agonistic CD40 antibodies and cancer therapy," Clin. Cancer Res. 19, 1035-43, 2013

Vonderheide et al., "Clinical activity and immune modulation in cancer patients treated with CP-870,893, a novel CD40 agonist monoclonal antibody," J Clin Oncol. 25, 876-83, 2007.

Wang et al., "Anaplastic lymphoma kinase (ALK) inhibitors: a review of design and discovery," Med. Chem. Commun. 5, 1266-79, 2014

Wang et al., "VISTA, a novel mouse Ig superfamily ligand that negatively regulates T cell responses," J. Exp. Med. 208, 577-92, 2011

Wittrup & Lieberman, "Knocking down disease: a progress report on siRNA therapeutics," Nat Rev Genet. 2015; 16:543-52.

Yang et al., "Oral vaccination with *salmonella* simultaneously expressing *Yersinia pestis* F1 and V antigens protects against bubonic and pneumonic plague,” J Immunol. 178, 1059-67, 2007

Ye et al., “T-cell exhaustion in chronic hepatitis B infection: current knowledge and clinical significance,” Cell Death Dis. Mar. 19; 6:e1694, 2015.

Young et al., “Co-inhibition of CD73 and A2AR Adenosine Signaling Improves Anti-tumor Immune Responses,” Cancer Cell 30, 391-403, 2016

Zarganes-Tzitzikas et al., “Inhibitors of programmed cell death 1 (PD-1): a patent review,” Expert Opinion on Therapeutic Patents 26, 973-77, published on-line Jul. 6, 2016

Zhan et al., “From monoclonal antibodies to small molecules: the development of inhibitors targeting the PD-1/PD-L1 pathway,” Drug Discovery Today 21, 1027-36, June 2016

Zorzi et al., “Acylated heptapeptide binds albumin with high affinity and application as tag furnishes long-acting peptides,” Nature Communications 8, 16092, 2017.

The invention claimed is:

1. An expression construct encoding up to four peptides selected from the group consisting of (i) a peptide consisting of the amino acid sequence SEQ ID NO:1; (ii) a peptide consisting of the amino acid sequence SEQ ID NO:2; (iii) a peptide consisting of the amino acid sequence SEQ ID NO:3; and (iv) a peptide consisting of the amino acid sequence SEQ ID NO:4.

2. The expression construct of claim 1, which encodes the peptide consisting of the amino acid sequence SEQ ID NO:2.

* * * * *

SEQUENCE LISTING

```
<160> NUMBER OF SEQ ID NOS: 5

<210> SEQ ID NO 1
<211> LENGTH: 20
<212> TYPE: PRT
<213> ORGANISM: Artificial Sequence
<220> FEATURE:
<223> OTHER INFORMATION: artificial peptide

<400> SEQUENCE: 1

Gln Thr Arg Thr Val Pro Met Pro Lys Ile His His Pro Pro Trp Gln
1               5                   10                  15

Asn Val Val Pro
            20

<210> SEQ ID NO 2
<211> LENGTH: 20
<212> TYPE: PRT
<213> ORGANISM: Artificial Sequence
<220> FEATURE:
<223> OTHER INFORMATION: artificial peptide

<400> SEQUENCE: 2

His His His Gln Val Tyr Gln Val Arg Ser His Trp Thr Gly Met His
1               5                   10                  15

Ser Gly His Asp
            20

<210> SEQ ID NO 3
<211> LENGTH: 21
<212> TYPE: PRT
<213> ORGANISM: Artificial Sequence
<220> FEATURE:
<223> OTHER INFORMATION: artificial peptide

<400> SEQUENCE: 3

Trp Asn Leu Pro Ala Ser Phe His Asn His His Ile Arg Pro His Glu
1               5                   10                  15

His Glu Trp Ile Gln
            20

<210> SEQ ID NO 4
<211> LENGTH: 20
<212> TYPE: PRT
```

```
<213> ORGANISM: Artificial Sequence
<220> FEATURE:
<223> OTHER INFORMATION: artificial peptide

<400> SEQUENCE: 4

Ser Ser Tyr His His Phe Lys Met Pro Glu Leu His Phe Gly Lys Asn
1               5                   10                  15

Thr Phe His Gln
            20

<210> SEQ ID NO 5
<211> LENGTH: 9
<212> TYPE: PRT
<213> ORGANISM: Plasmodium yoelii

<400> SEQUENCE: 5

Ser Tyr Val Pro Ser Ala Glu Gln Ile
1               5
```